United States Patent [19]

Numata et al.

[11] 4,239,758

[45] Dec. 16, 1980

[54] CEPHALOSPORINS

[75] Inventors: Mitsuo Numata; Masayoshi Yamaoka, both of Osaka; Isao Minamida, Kyoto; Mitsuru Shiraishi, Osaka; Tatsuo Nishimura, Hyogo, all of Japan

[73] Assignee: Takeda Chemical Industries, Ltd., Japan

[21] Appl. No.: 44,215

[22] Filed: May 31, 1979

Related U.S. Application Data

[62] Division of Ser. No. 783,230, Mar. 31, 1977, Pat. No. 4,172,891.

[30] Foreign Application Priority Data

Apr. 2, 1976 [JP] Japan .................................. 51/37374

[51] Int. Cl.³ ............................................ C07D 501/34
[52] U.S. Cl. ......................................... 424/246; 544/22; 544/25; 544/28; 544/27
[58] Field of Search ................. 544/22, 27, 25, 28; 424/246

[56] References Cited

U.S. PATENT DOCUMENTS 4,080,498 3/1978 Numata et al. .................... 544/27
4,098,888 7/1978 Ochiai et al. ..................... 544/27
4,172,891 10/1979 Numata et al. .................... 424/246

*Primary Examiner*—Nicholas S. Rizzo
*Attorney, Agent, or Firm*—Craig and Antonelli

[57] ABSTRACT

A novel cephalosporin derivative of the formula:

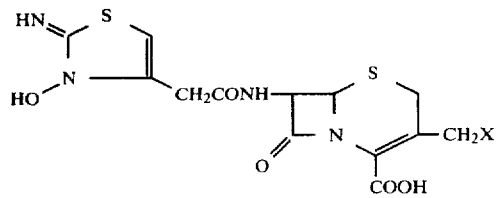

[wherein X is hydrogen, hydroxyl, acyloxy, alkoxy, carbamoyloxy, quaternary ammonium or a group of the formula $-SR^1$ (where $R^1$ is a nitrogen-containing heterocyclic group)] or a pharmaceutically acceptable salt or ester thereof is found to have potent antibiotic activity against various bacteria, particularly against gram-negative bacteria such as *Escherichia coli, Klebsiella pneumoniae, Proteus vulgaris, Proteus mirabilis, Proteus morganii, Proteus rettgeri* and *Citrobacter freundii.*

12 Claims, No Drawings

CEPHALOSPORINS

This is a division of application Ser. No. 783,230, filed Mar. 31, 1977, now U.S. Pat. No. 4,172,891.

This invention relates to novel antibiotic compounds which are useful as pharmaceuticals for treatment of diseases in fowls and animals including human beings, particularly of the infectious diseases caused by gram-positive and gram-negative bacteria, said antibiotic agents being cephalosporin derivatives having a novel 7-acyl group, which are of the general formula:

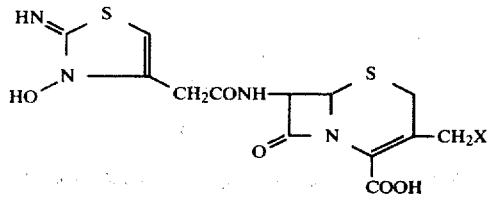

[wherein X is hydrogen, hydroxyl, acyloxy, alkoxy, carbamoyloxy, quaternary ammonium, or a group of the formula —$SR^1$ (where $R^1$ is a nitrogen-containing heterocyclic group)] or a pharmaceutically acceptable salt or ester thereof and also to a method of producing said cephalosporin derivatives.

The cephalosporin derivatives [I] are found to have potent antibiotic active against various bacteria, being particularly active against gram-negative bacteria including *Escherichia coli, Klebsiella pneumoniae, Proteus vulgaris, Proteus mirabilis, Proteus morganii, Proteus rettgeri* and *Citrobacter freundii*. Said cephalosporin derivatives display especially potent antibiotic activity against those mutant strains of aforementioned bacteria which possess β-lactamase (cephalosporinase) and are resistant to the known cephalosporins.

Referring to the above formula [I], X is an atom or a group including those known in the art as substituents bonded via methylene group at 3-position and preferably hydrogen, hydroxyl, acyloxy, alkoxy, carbamoyloxy, quaternary ammonium, or a group of the formula —$SR^1$ (where $R^1$ is a nitrogen-containing heterocyclic group).

Typical examples of acyloxy group include an alkylcarbonyloxy group of 2 to 4 carbon atoms such as acetyloxy or propionyloxy; an acetyloxy group substituted by an alkylcarbonyl group of 2 to 4 carbon atoms such as acetoacetyloxy or propionylacetyloxy; a phenylacetyloxy group which may be substituted at the α-position by, for example, hydroxy, sulfo or amino (e.g. mandeloxy, α-sulfo-phenylacetyloxy, phenylglycyloxy or phenylacetyloxy); an alkylcarbonyloxy group of 2 to 4 carbon atoms as substituted by a carboxyl group such as succinoyloxy, a group of the general formula:

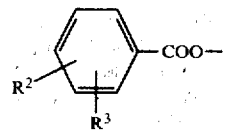

[wherein $R^2$ and $R^3$, respectively, mean hydrogen, carboxyl, carboethoxycarbamoyl, carboethoxysulfamoyl or nitro] (e.g. 2-carboxybenzoyloxy, 2-(carboethoxycarbamoyl)benzoyloxy, 2-(2-carboethoxysulfamoyl)benzoyloxy, 2-carboxy-3(or 4 or 6)-nitrobenzoyloxy or 2,4-dicarboxybenzoyloxy; and so on.

The alkoxy group may be a lower alkoxy having 1 to 4 carbon atoms such as methoxy or ethoxy.

As quaternary ammonium group represented by X, there may be mentioned a quaternary ammonium group of the general formula:

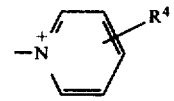

(wherein $R^4$ is hydrogen, methyl, carbamoyl, carboxyl, sulfonic or methoxy) which may be derived from pyridine derivatives such as pyridine, carbamoyl-substituted pyridine such as nicotinamide and isonicotinamide, carboxyl-substituted pyridine such as nicotinic acid and, isonicotinic acid, and sulfonic acid-substituted pyridine such as pyridine-sulfonic acid. Furthermore, X represents a group of the formula —$SR^1$ wherein $R^1$ is a nitrogen-containing heterocyclic group.

The nitrogen-containing heterocyclic group $R^1$ is normally exemplified by five- or six-membered nitrogen-containing heterocyclic groups which may optionally include 1 or more oxidized nitrogen atoms or such hetero-atoms as oxygen or/and sulfur in addition to nitrogen. Among such nitrogen-containing heterocyclic groups are six-membered heterocyclic nitrogen-containing groups containing one nitrogen atom such as pyridyl or N-oxidopyridyl; six-membered heterocyclic groups containing 2 nitrogen atoms such as pyrimidyl, pyridazinyl N-oxidopyridazinyl, etc. and; five-membered heterocyclic groups containing 2 nitrogen atoms such as pyrazolyl or diazolyl (i.e. imidazoyl); five-membered heterocyclic groups containing one nitrogen atom and one sulfur atom such as thiazolyl; five-membered heterocyclic groups containing 2 nitrogen atoms and one sulfur atom such as 1,2,3-thiadiazolyl, 1,2,4-thiadiazolyl, 1,3,4-thiadiazolyl and 1,2,5-thiadiazolyl; five-membered heterocyclic groups containing 2 nitrogen atoms and one oxygen atom such as 1,2,3-oxadiazolyl, 1,2,4-oxadiazolyl, 1,3,4-oxadiazolyl and 1,2,5-oxadiazolyl; five-membered heterocyclic groups containing 3 nitrogen atoms such as 1,2,3-triazolyl and 1,2,4-triazolyl; and five-membered heterocyclic groups containing 4 nitrogen atoms such as 1H-tetrazolyl and 2H-tetrazolyl. Such nitrogen-containing heterocyclic groups may have substituents, said substituent being monovalent group such as lower alkyl having 1 to 4 carbon atoms, e.g. methyl, ethyl, trifluoromethyl, propyl, isopropyl, butyl, isobutyl, etc.; lower alkoxy having 1 to 4 carbon atoms, e.g. methoxy, ethoxy, propoxy, isopropoxy, butoxy, etc.; halogen, e.g. chlorine, bromine, etc.; hydroxyl; mercapto; amino; carboxyl; carbamoyl; etc.; and various substituents which are attached via polyvalent groups such as lower alkylene groups having 1 to 4 carbon atoms, -S-,

or so. Where the polyvalent group is a lower alkylene group, the substituent may for example be hydroxyl, mercapto, amino, guanyl, morpholino, carboxyl, sulfo, carbamoyl, alkoxycarbonyl, lower alkylcarbamoyl, alkoxy, alkylthio, alkylsulfonyl, acyloxy or morpholinocarbonyl. Where the polyvalent group is -S- or

the substituent may for example be a lower alkyl group or a lower alkylene group having one of the aforementioned substituent groups. Where said polyvalent group is

there may also be directly attached such substituents as carboxyl, alkoxycarbonyl, acyl, carbamoyl, lower alkylcarbamoyl, di- or tri- lower-alkylamino etc. More specifically, there may be mentioned, among others, substituted alkyls such as carboxymethyl, carbamoylmethyl, a poly-N-lower alkylcarbamoylmethyl (e.g. N,N-dimethylcarbamoylmethyl), hydroxylower-alkyl (e.g. hydroxymethyl, 2-hydroxyethyl), acyloxy-lower alkyl (e.g. acetoxymethyl, 2-acetoxyethyl), alkoxycarbonylmethyl (e.g. methoxycarbonylmethyl, ethoxycarbonylmethyl, propoxycarbonylmethyl), methylthiomethyl, methylsulfonylmethyl, a poly-N-lower alkylamino-lower alkyl (e.g. N,N-dimethylaminomethyl, N,N-dimethylaminoethyl, N,N,N-trimethylammoniumethyl), morpholinomethyl, guanylmethyl, guanylethyl, etc.; substituted amino groups such as lower alkylamino (e.g. methylamino), sulfo-lower alkylamino (e.g. 2-sulfoethylamino), hydroxy-lower alkylamino (e.g. hydroxyethylamino), lower alkylamino-lower alkylamino (e.g. 2-dimethylaminoethylamino, 2-trimethylammoniumethylamino), acylamino (e.g. acetylamino), 2-dimethylaminoacetylamino, 2-trimethylammoniumacetylamino, lower alkoxycarbonylamino (e.g. methoxycarbonylamino, etc.); substituted thio groups such as methylthio, 2-hydroxyethylthio, 2-acyloxyethylthio (e.g. 2-acetoxyethylthio, 2-phenylacetoxyethylthio, 2-caproyloxyethylthio), carboxymethylthio, alkoxycarbonylmethylthio (e.g. methoxycarbonylmethylthio, ethoxycarbonylmethylthio, propoxycarbonylmethylthio), carbamoylmethylthio, N-lower alkylcarbamoylmethylthio (e.g. N,N-dimethylcarbamoylmethylthio), acetylmethylthio, N-lower alkylamino-lower alkylthio (e.g. 2-N,N-dimethylaminoethylthio, 2-N,N,N-trimethylammoniumethylthio), morpholinocarbonylmethylthio, 2-sulfoethylthio, etc. Among the substituents as mentioned above, lower alkyl groups such as methyl or lower alkylene groups having 1 to 2 carbon atoms substituted by a substituent, for example, carboxymethyl, hydroxymethyl, dimethylaminoethyl, carbamoylmethyl, etc. are especially preferred.

The present invention also provides a process for producing the cehalosporin derivative [I], which comprises reacting a compound of the formula:

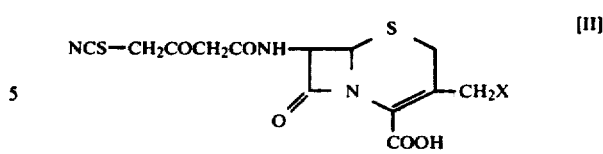

[wherein X has the same meaning as defined hereinabove] with hydroxylamine or, alternatively, by reacting a compound of the general formula:

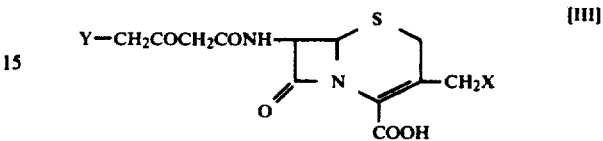

[wherein X has the same meaning as hereinbefore defined; Y is halogen] with thiocyanic acid and hydroxylamine. A compound of the general formula [I] wherein X is a quaternary ammonium group or a group of the formula —SR$^1$ (where R$^1$ has the same meaning as defined hereinbefore) is obtainable also by reacting a compound of the general formula:

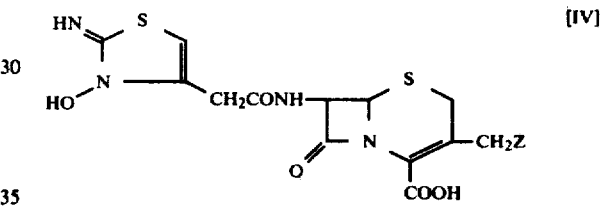

[where Z is acyloxy] with a pyridine compound or a thiol compound of the general formula R$^1$SH (wherein the symbol R$^1$ has the same meaning as hereinbefore defined). The acyloxy represented by Z includes those as mentioned above in connection with acyloxy represented by X.

The cephalosporin derivative [I] according to this invention can be produced by reacting a compound [II] with hydroxylamine. The compound [II] may be reacted normally in its free form or as an organic or inorganic salt at the carboxyl function, such as the salts of alkali or alkaline earth metals, e.g. lithium, sodium, potassium, etc., or the salt of triethylamine or of organic or inorganic acid, e.g. hydrochloric acid, sulfuric acid, etc. The hydroxylamine is normally reacted as the salt of a mineral acid, e.g. hydrochloric acid, sulfuric acid or phosphoric acid, or the salt of an organic acid, e.g. oxalic acid, acetic acid or p-toluenesulfonic acid.

Normally the reaction proceeds advantageously in a solvent which is preferably one that will not interfere with the reaction. Thus, there may be mentioned the common solvents which are not likely to react with the ketonic reagent (e.g. hydroxylamine) such as water, methanol, ethanol, dioxane, acetonitrile, tetrahydrofuran, chloroform, methylene chloride, ethylene chloride, dimethylformamide, dimethylacetamide and hexamethyl phosphoramide as well as various mixtures of such solvents. While it is normally sufficient to employ an equimolar amount of hydroxylamine relative to the compound [II], it is preferable to use a slight excess, e.g. 1.1 equivalents, of hydroxylamine. This reaction normally proceeds under acidic conditions, preferably in the concomitant presence of an acid of the variety mentioned hereinbefore. Since hydroxylamine is normally employed in the form of an acid salt, it is then not necessary to add an acid independently, although there are instances in which the addition of a molecular equivalent of such acid would lead to more satisfactory results. To let the reaction proceed with greater facility, generally the reaction system is desirably maintained within the range of pH 0.5 to 7.0 and, for better results, within the range of 3.0 to 6.0. While the reaction temperature is not particularly critical, normally the reaction is desirably conducted at room temperature or within the range of 0° to 80° C., particularly at temperatures not exceeding 60° C. The reaction is normally carried out for 0.5 to 24 hours, preferably 0.5 to 12 hours at room temperature. The resultant cephalosporin derivative [I] may be isolated and purified by known procedures such as solvent extraction, pH change, phasic transfer, crystallization, recrystallization and chromatography.

The cephalosporin derivative [I] may be produced by reacting a compound [III] with thiocyanic acid and hydroxylamine. The compound [III] is reacted in its free form or as the salt of an alkali metal, alkaline earth metal or organic or inorganic acid just as those hereinbefore described in compound [II]. Hydroxylamine is employed in its free form or as the above-mentioned salt of a mineral acid or organic acid. Thiocyanic acid is reacted in such forms as the salt of an alkali metal, e.g. potassium, sodium, calcium or lithium, the salt of an alkaline earth metal or the ammonium salt. In conducting the reaction, whichever of thiocyanic acid and hydroxylamine may be reacted with compound [III] in the first place or both of them may be reacted at the same time with compound [III]. The proportions of thiocyanic acid and hydroxylamine are each either equimolar or a slight excess, preferably about 1.1 molar equivalents, relative to the compound [III]. The reaction is generally conducted in a solvent which is normally one of those solvents employed in the reaction of compound [II] with hydroxylamine. The pH, temperature, time and other conditions at the reaction desirably approximate those employed for the reaction of compound [II] with hydroxylamine. The resultant cephalosporin derivative [I] may be isolated and purified by the known procedures mentioned hereinbefore.

The contemplated cephalosporin derivative [I] may also be produced from a compound [IV] by conventional procedures generally classified as the nucleophilic substitution reaction of the 3-acyloxy group which comprises, for example, reacting a compound [IV] with a pyridine compound of the general formula:

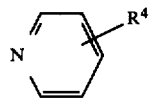

[wherein the symbol has the same meaning as hereinbefore defined] or a thiol compound of the general formula:
$R^1SH$

[wherein the symbol has the meaning hereinbefore defined]

The nucleophilic substitution reaction of a compound [IV] with a pyridine compound or a thiol $R^1SH$ into a compound [I] is conducted by mixing them in a solvent.

The compound [IV] may be used as a free form or a salt with an alkali metal such as sodium or potassium. The thiol $R^1SH$ to be employed is subjected to the reaction in its free form or as a salt at its thiol function with an alkali metal such as sodium or potassium. The reactant, a pyridine compound or a thiol $R^1SH$, is used in the amount of 1 to 4 equivalents relative to [IV]. This reaction is usually effected by heating at 40° to 80° C. in the neighbourhood of neutrality for 1 to 20 hours. The reaction is carried out in a solvent, preferred examples of which are water and aqueous solvents such as mixtures of water with highly polar solvents which will not interfere with the reaction, e.g. acetone, tetrahydrofuran, dimethylformamide, methanol, ethanol, dimethylsulfoxide, etc. To maintain the pH of the reaction medium around the neutral pH, a proper amount of a base such as sodium hydrogen carbonate, potassium hydrogen carbonate or the like or an acid such as hydrochloric acid, phosphoric acid or the like may be added to the medium. If necessary, a buffer solution may also be employed. The cephalosporin [I] thus resulted can be isolated and purified by conventional procedures similar to those hereinbefore described. [refer also to the literatures: Cephalosporin and Penicillin, ed. E. H. Flynn, Chapter 4, Part 5, p. 151 (1972), Academic Press; German Patent Application OLS No. 1795727, German Pat. Nos. 1745624, 1795484, 1445684, 1445701, 1795615, 1795600, and 1445828, and German Patent Applications OLS Nos. 2607064 (laid open on Sept. 2, 1976) and 2461478 (laid open on Feb. 26, 1976), etc.]

The compounds [II] and [III] which are employed as starting materials in the present invention may each be commercially produced from the common raw materials in the cephalosporin industry, e.g. cephalosporin C, desacetylcephalosporin C, or 7-aminocephalosporins which are commercially obtainable from either of said compounds, for example by the procedures described in Japanese Patent Application Laid-Open No. 95293/1975 and No. 111093/1975, Patent Application No. 1274/1976 and other literature or by procedures analogous thereto. The compound [III] wherein X is carbamoyloxy is novel and useful intermediate for production of the cephalosporin derivative [I], and especially preferred in the present invention. Representative procedures for preparing those compounds are shown in the reference examples described hereinafter.

The cephalosporin derivative [I] thus obtained may be put to use with its 4-carboxyl group remaining unmodified and free or, alternatively, modified, for example, in the form of salt with a nontoxic cation such as sodium, potassium or the like, a basic amino acid such as arginine, ornithine, lysine or histidine, or a polyhydroxymethylaminomethane such as N-methylglucamine, diethanolamine, triethanolamine or tris-hydroxymethylaminomethane. The 4-carboxyl group may also be esterified so that said derivative [I] will be converted to a biologically active ester derivative which would be conductive to an increased blood level or/and a prolonged efficacy. As examples of the effective ester residues useful for such purposes may be mentioned alkoxymethyl groups such as methoxymethyl, ethoxymethyl, isopropoxymethyl, α-methoxyethyl, α-ethoxyethyl, etc.; α-alkoxy-α-substituted methyl groups such as α-alkoxyethyl; alkylthiomethyl groups such as methylthiomethyl, ethylthiomethyl, isopropylthiomethyl, etc.; acyloxymethyl or α-acyloxy-α-substituted methyl groups such as pivaloyloxymethyl, α-acetoxybutyl, etc.;

and α-alkoxycarbonyloxy-α-substituted methyl groups such as ethoxycarbonyloxymethyl, α-ethoxycarbonyloxyethyl, etc. Furthermore, the cephalosporin derivative [I] may alternatively in the form of a salt at the basic position such as imino group of 3-position thereof with an acid such as a mineral acid (e.g. hydrochloric acid, sulfuric acid, phosphoric acid) or an organic sulfonic acid (e.g. methanesulfonic acid).

The contemplated product cephalosporin derivatives [I] may be administered in the same manner as known cephalosporins, for example in bulk form or, as formulated with physiologically acceptable carriers or vehicles in the routine manner, in such dosage forms as solutions and suspensions. More specifically, the present derivatives [I] are used as safe drugs for the treatment of the inflammatory diseases, pustular diseases, respiratory organ infections, bile duct infections, intestinal infections, urinary tract infections, gyneobsteric infections and other diseases as caused by the aforementioned bacteria. The following derivatives of this invention, among others, are administered either intramuscularly or intravenously at a daily dose of about 5 to 20 mg per Kg body weight of adult human in 3 to 4 divided doses: sodium 7-[2-(2-imino-3-hydroxy-4-thiazolin-4-yl)acetamido]-3-(1-methyltetrazol-5-yl)thiomethyl-3-cephem-4-carboxylate; 7-[2-(2-imino-3-hydroxy-4-thiazolin-4-yl)acetamido]-3-[1-N,N-dimethylaminoethyl)tetrazol-5-yl]thiomethyl-3-cephem-4-carboxylic acid betaine; sodium 7-[2-(2-imino-3-hydroxy-4-thiazolin-4-yl)acetamido]-3-(1-carbamoylmethyltetrazol-5-yl)thiomethyl-3-cephem-4-carboxylate; sodium 7-[2-(2-imino-3-hydroxy-4-thiazolin-4-yl)acetamido]-3-(1,3,4-thiadiazol-2-yl)thiomethyl-3-cephem-4-carboxylate; sodium 7-[2-(2-imino-3-hydroxy-4-thiazolin-4-yl)acetamido]-3-(2-methyl-1,3,4-thiadiazol-5-yl)thiomethyl-3-cephem-4-carboxylate; 7-[2-(2-imino-3-hydroxy-4-thiazolin-4-yl)acetamido]-3-[2-(2-N,N-dimethylaminoethyl)-1,3,4-thiadiazol-5-yl]thiomethyl-3-cephem-4-carboxylic acid betaine; sodium 7-[2-(2-imino-3-hydroxy-4-thiazolin-4-yl)acetamido]-3-(2-hydroxymethyl-1,3,4-thiadiazol-5-yl)thiomethyl-3-cephem-4-carboxylate; sodium 7-[2-(2-imino-3-hydroxy-4-thiazolin-4-yl)acetamido]-3-(2-N,N-dimethylcarbamoylmethyl-1,3,4-thiadiazol-5-yl)thiomethyl-3-cephem-4-carboxylate; sodium 7-[2-(2-imino-3-hydroxy-4-thiazolin-4-yl)acetamido]-3-[2-(2-hydroxyethylthio)-1,3,4-thiadiazol-5-yl]thiomethyl-3-cephem-4-carboxylate, disodium 7-[2-(2-imino-3-hydroxy-4-thiazolin-4-yl)acetamido]-3-(2-carboxymethyl-1,3,4-thiadiazol-5-yl)thiomethyl-3-cephem-4-carboxylate, sodium 7-[2-(2-imino-3-hydroxy-4-thiazolin-4-yl)acetamido]-3-(1,2,3-triazol-4-yl)thiomethyl-3-cephem-4-carboxylate, sodium 7-[2-(2-imino-3-hydroxy-4-thiazolin-4-yl)acetamido]-3-(3,4-dimethyl-1,2,4-triazol-5-yl)thiomethyl-3-cephem-4-carboxylate, sodium 7-[2-(2-imino-3-hydroxy-4-thiazolin-4-yl)acetamido]-3-(3-hydroxymethyl-4-methyl-1,2,4-triazol-5-yl)thiomethyl-3-cephem-4-carboxylate, sodium 7-[2-(2-imino-3-hydroxy-4-thiazolin-4-yl)acetamido]-3-(2-methyl-1,3,4-oxadiazol-5-yl)thiomethyl-3-cephem-4-carboxylate, sodium 7-[2-(2-imino-3-hydroxy-4-thiazolin-4-yl)acetamido]-3-(3-methyl-1,2,4-thiadiazol-5-yl)thiomethyl-3-cephem-4-carboxylate, sodium 7-[2-(2-imino-3-hydroxy-4-thiazolin-4-yl)acetamido]-3-[1-(2-hydroxyethyl)-1H-tetrazol-5-yl]thiomethyl-3-cephem-4-carboxylate, and disodium 7-[2-(2-imino-3-hydroxy-4-thiazolin-4-yl)acetamido]-3-(4-carboxymethylthiazol-2-yl)thiomethyl-3-cephem-4-carboxylate.

The following examples are further illustrative of the production method of this invention.

In these examples, the NMR spectra were determined by means of a Varian HA 100 (100 MHz) or T 60 (60 MHz) spectrophotometer with tetramethylsilane as the reference and expressed in δ(ppm). The symbol s means a singlet, d a doublet, t a tripplet, q a quartet, m a multiplet and J a coupling constant.

Following each example is a tabulation of the minimal inhibitory concentrations (MIC) of the present compound [I] obtained in accordance with the particular example against several representative gram-negative bacteria and the corresponding concentrations of cephaloridine [7-(2-thienylacetamido)-3-(1-pyridyl)-methyl-3-cephem-4-carboxylic acid betaine] and cefazolin [sodium 7-(1H-tetrazol-1-yl)acetamido-3-(2-methyl-1,3,4-thiadiazol-5-yl)thiomethyl-3-cephem-4-carboxylate], both of which are typical cephalosporins commercially available and clinically accepted nowadays [The New England Journal of Medicine 294, 24 (1976) and Journal of Pharmaceutical Science 64, 1899 (1975)]. There are also shown the effective doses of the typical compounds of this invention on the mice infected with *Escherichia coli* in comparison with that of cephaloridine.

REFERENCE EXAMPLE 1

Production of 7-(4-chloro-3-oxobutyrylamido)-3-acetoxymethyl-3-cephem-4-carboxylic acid A solution of 4.4 g of diketene in 10 ml of methylene chloride is cooled to −35° C. and 3.92 g of chlorine is bubbled into the solution. The solution is stirred for 15 minutes. Separately, 10.9 g of 7-aminocephalosporanic acid and 8.1 g of triethylamine are dissolved in 100 ml of methylene chloride and the solution is cooled to −30° C. To the latter solution is added the former solution under stirring and cooling so that the temperature of the mixture will not exceed −30° C. The temperature of the solution is gradually increased to room temperature over an hour, after which the solvent is distilled off under reduced pressure. To the residue is added 100 ml of ethyl acetate and the mixture is shaken vigorously with 100 ml of a 10% aqueous solution of phosphoric acid. The water layer is taken, saturated with sodium chloride and extracted three times with ethyl acetate. The ethyl acetate layers are pooled, washed with a saturated aqueous solution of sodium chloride and, after drying, concentrated under reduced pressure to 20 ml. The concentrate is allowed to stand in the cold, whereupon crystals formed. The crystals are recovered by filtration. By the above procedure is obtained 6.3 g of the captioned compound.

m.p. 135°–140° C. (decomp.).

IR(cm$^{-1}$, KBr): 1790, 1750, 1655.

NMR (100 MHz, d$_6$-DMSO, δ): 2.00 (s, COCH$_3$) 3.41 & 3.64 (ABq, J=18 Hz, 2-CH$_2$), 3.56 (s, COCH$_2$CO), 4.50 (s, ClCH$_2$—), 4.67 & 5.00 (ABq, J=18 HZ, 3-CH$_2$), 5.07 (d, J=4.5 Hz, 6-H), 5.66 (dd, J=4.5 & 8 Hz, 7-H), 9.04 (d, J=8 Hz, CONH).

Elemental analysis: Calcd. for C$_{14}$H$_{15}$ClN$_2$O$_7$S C; 43.03; H; 3.87, N; 7.17. Found C; 43.01, H; 3.89, N; 7.18.

REFERENCE EXAMPLE 2

Production of 7-(4-bromo-3-oxobutyrylamino)-3-acetoxymethyl-3-cephem-4-carboxylic acid A solution of 3.4 g of diketene in 10 ml of methylene chloride is cooled to −30° C. and, then, a solution of 6.4 g of bromine in 10 ml of methylene chloride is added dropwise. Separately, 10.9 g of 7-amimnocephalosporanic acid and 8.1 g of triethylamine are dissolved in 100 l of methylene chloride and the solution is cooled to −30° C. To this solution is added the former reaction mixture under stirring and cooling so that the temperature of the system will not exceed −30° C. The temperature of the system is then allowed to increase gradually to room temperature over an hour, after which the solvent is distilled off under reduced pressure. To the residue is added 100 ml of ethyl acetate and the mixture is shaken with 100 ml of a 10% aqueous solution of phosphoric acid. The water layer is taken, saturated with sodium chloride and extracted twice with ethyl acetate. The ethyl acetate layers are pooled, washed with a saturated aqueous solution of sodium chloride, dried, treated with activated carbon and concentrated to dryness under reduced pressure. To the residue is added ether and the mixture is allowed to stand. The resultant crystals are recovered by filtration under suction to obtain the captioned compound. This product includes ½ mole of ethyl acetate as the solvent of crystallization. Yield 8 g.

IR(cm$^{-1}$, KBr): 1780, 1735, 1650.

NMR(100 MHz, d$_6$-DMSO, δ): 2.01 (s, CH$_3$CO), 3.54 (m, 2-CH$_2$), 3.62 (s, COCH$_2$CO), 4.37 (s, Br, CH$_2$CO), 4.67 & 5.01 (ABq, J=14 Hz, 3-CH$_2$), 5.08 (d, J=4 Hz, 6-H), 5.66 (dd, J=4 & 8 Hz, 7-H), 9.04 (d, J=8 Hz, CONH)

Elemental analysis: Calcd. for C$_{14}$H$_{15}$BrN$_2$O$_7$S.½C$_4$H$_8$O$_2$ C; 39.40, H; 3.75, N; 6.13. Found: C; 39.20, H; 3.63, N; 6.09.

REFERENCE EXAMPLE 3

Production of 7-(4-bromo-3-oxobutyrylamido)-3-(mandeloxymethyl)-3-cephem-4-carboxylic acid A solution of 1.34 g (0.013 mole) of diketene in 10 ml of methylene chloride is cooled to −30° C. and a solution of 3.14 g (0.014 mole) of bromine in 10 ml of methylene chloride is added dropwise. Separately, 3.6 g (0.01 mole) of 7-amino-3-(mandeloxymethyl)-3-cephem-4-carboxylic acid and 2.8 ml (0.02 mole) of triethylamine are dissolved in 50 ml of methylene chloride and the solution is cooled to −20° C. To this solution is added dropwise the above reaction mixture over a period of 10 minutes. The cooling bath is removed to let the temperature of the mixture return to room temperature, followed by stirring for another 30 minutes. The methylene chloride is distilled off under reduced pressure. To the residue are added 30 ml of 10% phosphoric acid, 100 ml of water, 20 ml of tetrahydrofuran and 250 ml of ethyl acetate, and the mixture is shaken vigorously. The organic layer is taken, washed with water and dried. The solvent is distilled off under reduced pressure. Then, with the addition of 200 ml of ether, the vessel wall is rubbed, whereupon the captioned compound is obtained as a powder. Yield 4.5 g.

IR(KBr, cm$^{-1}$): 3370, 1782, 1736, 1672, 1648, 1539.

NMR(100 MHz, d$_6$-DMSO, δ): 3.24(broad s, 2-CH$_2$), 3.63 (s, CH$_2$CO), 4.39 (s, BrCH$_2$—), 4.77 & 5.05 (ABq, J=14 Hz, 3-CH$_2$), 5.04 (d, J=5 Hz, 6-H), 5.17 (s, $$-\mathrm{CH}-),$$

5.68 (dd, J=5 & 8 Hz, 7-H), 7.3–7.5 (m, 5H, C$_6$H$_5$—), 9.02 (d, J=8 Hz, CONH).

REFERENCE EXAMPLE 4

Production of 7-(4-chloro-3-oxobutyrylamido)-3-(1-methyltetrazol-5-yl)thiomethyl-3-cephem-4-carboxylic acid While a solution of 166.5 g (1.98 moles) of diketene in 830 ml of methylene chloride is stirred under cooling to keep the internal temperature between −25° C. and −30° C., 140 g (1.97 moles) of chlorine gas is bubbled into the solution. The system is then stirred at the same temperature for 30 minutes. Separately, 500 g (1.52 moles) of 7-amino-3-(1-methyltetrazol-5-yl)thiomethyl-3-cephem-4-carboxylic acid and 394 g (3.05 moles) of dibutylamine are dissolved in 3 l of methylene chloride and the solution is cooled to −10° C. ~ −20° C. To this solution is added dropwise the above reaction mixture over 30 minutes, after which time the mixture is stirred for 40 minutes. The reaction mixture is added to a mixture of 6 l of ethyl acetate and 6 l of 10% phosphoric acid, followed by vigorous stirring. The organic layer is washed with water, dried and concentrated to dryness under reduced pressure. The residue is loosened with ether to obtain the captioned compound as a powder. Yield 644 g.

IR(KBr, cm$^{-1}$): 1783, 1732, 1679.

NMR(100 MHz, d$_6$-DMSO, δ): 3.57 & 3.79 (ABq, J=18 Hz, 2-CH$_2$), 3.56 (s, COCH$_2$CO), 3.91 (s, tetrazole-CH$_3$), 4.20 & 4.37 (ABq, J=13 Hz, 3-CH$_2$), 4.52 (s, ClCH$_2$), 5.07 (d, J=5 Hz, 6-H), 5.67 (dd, J=5 & 8 Hz, 7-H), 9.05 (d, J=8 Hz, —CONH—).

REFERENCE EXAMPLE 5

Production of 7-(4-bromo-3-oxobutyrylamido)-3-(1-methyltetrazol-5-yl)thiomethyl-3-cephem-4-carboxylic acid A solution of 1.03 g (0.012 mole) of diketene in 5 ml of methylene chloride is cooled to −30° C. and a solution of 2.24 g (0.014 mole) of bromine in 5 ml of methylene chloride is added dropwise. Separately, 3.29 g (0.01 mole) of 7-amido-3-(1-methyltetrazol-5-yl)thiomethyl-3-cephem-4-carboxylic acid and 2.02 g of triethylamine is dissolved in 20 ml of methylene chloride and the solution is cooled to −20° C. To this solution is added dropwise the above reaction mixture over a short time, whereupon the temperature of the mixture increases to 0° C. The temperature is allowed to increase gradually to room temperature, followed by stirring for 15 minutes. The reaction mixture is added to a mixture of 150 ml of ethyl acetate and 100 ml of 10% phosphoric acid.

After vigorous stirring, the organic layer is washed with water, dried and concentrated to dryness under reduced pressure. The residue is loosened with ether, whereupon the captioned product is obtained as a powder. Yield 4.1 g.

IR(KBr, cm$^{-1}$): 1780, 1725, 1674.

NMR(100 MHz, d$_6$-DMSO, δ): 3.59 & 3.81 (ABq, J=18 Hz, 2-CH$_2$), 3.63 (s, COCH$_2$CO), 3.93 (s, tetrazole-CH$_3$), 4.21 & 4.38 (ABq, J=13 Hz, 3-CH$_2$), 4.38 (s, BrCH$_2$), 5.07 (d, J=5 Hz, 6-H), 5.67 (q, J=5 & 8 Hz, 7-H), 9.06 (d, J=8 Hz, CONH).

REFERENCE EXAMPLE 6

Production of 7-(4-bromo-3-oxobutyrylamido)-3-(carbamoyloxymethyl)-3-cephem-4-carboxylic acid A solution of 0.101 g of diketene in 2 ml of methylene chloride is cooled to −30° C. and a solution of 0.208 g of bromine in 1.3 ml of carbon tetrachloride is added dropwise. Separately, 0.273 g of 7-amino-3-(carbamoyloxymethyl)-3-cephem-4-carboxylic acid and 0.303 g of triethylamine are dissolved in 4 ml of methylene chloride and the solution is cooled to −20° C. To this solution is added dropwise the above reaction mixture. The cooling bath is then removed to allow the temperature of the reaction mixture to rise to room temperature, followed by stirring for 30 minutes. The methylene chloride is distilled off under reduced pressure and the residue is shaken vigorously with 20 ml of 10% phosphoric acid, 30 ml of methyl ethyl ketone and 5 ml of a saturated aqueous solution of sodium chloride. The organic layer is taken, washed with 5 ml of a saturated aqueous solution of sodium chloride and dried. The solvent is then distilled off under reduced pressure. With the addition of 5 ml of ether, the vessel wall is rubbed to obtain the captioned compound as a powder. Yield 0.148 g.

IR(Kbr, cm$^{-1}$): 3390, 3000, 1780, 1740, 1550, 1400,1, 1330.

UVλmax(ε in water): 262 nm (0.89×10$^4$).

NMR(100 MHz, d$_6$-DMSO, δ): 3.43 & 3.66 (ABq, J=18 Hz, 2-CH$_2$), 3.64 (s, COCH$_2$CO), 4.40 (s, BrCH$_2$), 4.64 & 4.93 (ABq, J=13 Hz, 3-CH$_2$), 5.11 (d, J=5 Hz, 6-H), 5.68 (dd, J=5 & 9 Hz, 7-H), 6.5 (broad s, OCONH$_2$), 9.04 (d, J=9 Hz, CONH).

Elemental analysis: Calcd. for C$_{13}$H$_{14}$N$_3$O$_7$SBr: C; 35.79, H; 3.23, N; 9.61. Found C; 35.84, H; 3.25, N; 8.26.

REFERENCE EXAMPLE 7

Production of 7-(4-thiocyanato-3-oxobutyrylamido)-3-acetoxymethyl-3-cephem-4-carboxylic acid In 10 ml of acetonitrile is dissolved 0.39 g (1 M mole) of 7-(4-chloro-3-oxobutyrylamido)-3-acetoxymethyl-3-cephem-4-carboxylic acid together with potassium thiocyanate (1.5 M moles) and the solution is stirred at room temperature for 16 hours. The solvent is distilled off under reduced pressure and 10 ml of a saturated aqueous solution of sodium chloride is added. The mixture is made acidic with 50% phosphoric acid and extracted with ethyl ester. The extract is washed with a saturated aqueous solution of sodium chloride and dried. The solvent is distilled off under reduced pressure and the residue is loosened up with ether. The resultant powder is recovered by filtration. By the above procedure is obtained the captioned compound. This product includes ½ mole of ether as the solvent of crystallization. Yield 0.39 g (94%).

IR(KBr, cm$^{-1}$): 2350(CN), 1785, 1730.

NMR(100 MHz, d$_6$-DMSO, δ): 2.01 (s, COCH$_3$), 3.42 & 3.66 (ABq, J=18 Hz, 2-CH$_2$), 3.62 (s, COCH$_2$CO), 4.37 (s, SCH$_2$CO), 4.68 & 5.00 (ABq, J=12 Hz, 3-CH$_2$), 5.09 (d, J=4.5 Hz, 6-H), 5.67 (dd, J=4.5 & 8 Hz, 7-H), 9.06 (d, J=8 Hz, CONH).

Elemental analysis: Calcd. for C$_{15}$H$_{15}$N$_3$O$_7$S$_2$•0.5(C$_2$H$_5$)$_2$O C; 43.11, H; 3.52, N; 9.50. Found: C; 42.98, H; 3.74, N; 9.44.

EXAMPLE 1

Production of sodium 7-[2-(2-imino-3-hydroxy-4-thiazolin-4-yl)acetamido]-3-acetoxymethyl-3-cephem-4-carboxylate In a mixture of 10 ml of water and 10 ml of tetrahydrofuran is dissolved 1.653 g of 7-(4-thiocyanato-3-oxobutyrylamido)-3-acetoxymethyl-3-cephem-4-carboxylic acid together with 0.336 g of sodium hydrogen carbonate and the solution is stirred at room temperature. To this mixture is added 0.278 g of hydroxylamine hydrochloride followed by stirring for 3 hours. The reaction mixture is allowed to stand in the refrigerator for 15 hours, after which it is concentrated under reduced pressure to remove the tetrahydrofuran. To the residue is added 0.336 g of sodium hydrogen carbonate and the resultant mixture is subjected to column chromatography on polystyrene resin (Amberlite YAD-2 ®, Rohm & Haas Co.) with water as the developer. The fractions containing the contemplated product are pooled and lyophilized. By the above procedure is obtained the captioned compound. Yield 0.382 g.

IR(KBr, cm$^{-1}$): 1765, 1610, 1390, 1240.

NMR(100 MHz, D$_2$O, δ): 2.17 (s, CH$_3$CO), 3.41 & 3.73 (ABq, J=18 Hz, 2-CH$_2$), 3.79 (s, CH$_2$CO), 5.17 (d, J=4.5 Hz, 6-H), 5.76 (d, J=4.5 Hz, 7-H), 6.74 (s, thiazolin 5-H).

UVλmax(ε, in H$_2$O): 260 nm(1.147×10$^4$).

Elemental analysis: Calcd. for C$_{15}$H$_{15}$N$_4$O$_7$S$_2$Na•1.5-H$_2$O C; 37.73, H; 3.80, N; 11.73. Found: C; 37.50, H; 3.85, N; 11.29.

| Minimum Inhibitory Concentrations (mcg/ml, agar dilution) | | | |
|---|---|---|---|
| Strain of bacterium | Present compound | Cephaloridine | Cefazolin |
| E. coli NIHJ | 0.20 | 6.25 | 1.56 |
| E. coli 0-111 | 0.10 | 3.13 | 1.56 |
| E. coli T-7 | 3.13 | >100 | >100 |
| K. pneumoniae DT | 0.10 | 3.13 | 1.56 |
| K. pneumoniae GN 3835 | 0.20 | 50 | 12.5 |
| P. vulgaris IFO 3988 | 0.39 | 6.25 | 3.13 |
| P. mirabilis GN 4359 | 0.20 | 3.13 | 3.13 |
| P. morganii IFO 3168 | 0.39 | >100 | >100 |
| P. rettgeri 8(TNO 336) | ≦0.03 | 1.56 | 0.20 |
| P. rettgeri GN 4733 | 0.10 | >100 | >100 |
| Ent. cloacae IFO 12937 | 12.5 | >100 | >100 |
| Cit. freundii GN 99 | 1.56 | 50 | 50 |
| Cit. freundii GN 1706 | 3.13 | >100 | >100 |

EXAMPLE 2

Production of 7-[2-(2-imino-3-hydroxy-4-thiazolin-4-yl)acetamido]-3-acetoxymetyl-3-cephem-4-carboxylic acid In 10 ml of dimethylacetamide is dissolved 3.9 g of 7-(4-chloro-3-oxobutyrylamido)-3-acetoxymethyl-3-cephem-4-carboxylic acid together with 1.0 g of potassium thiocyanate and the solution is allowed to stand at room temperature for 15 hours. To this mixture is added 0.7 g of hydroxylamine hydrochloride and the mixture is heated at 57° C. for 2 hours. After cooling, 40 ml of ethyl ether is added to this reaction mixture, whereupon an oily product separates out. The supernatant fluid is removed by decantation and the residue is mixed with 100 ml of ethyl acetate. The wall of the vessel is then rubbed, whereby the oil is converted to a powder. This powder is recovered by filtration under suction. By the above procedure is obtained 6.0 g of the captioned compound as a crude powder. A 1-gram portion of the above crude powder is dissolved in 50 ml of a 10% aqueous solution of sodium hydrogen carbonate and the solution is filtered under suction. The filtrate is adjusted to pH 3 with acetic acid and concentrated under reduced pressure to about 2 ml. The concentrate is allowed to stand in a refrigerator. The resultant crystalline powder is recovered by filtration and dried. By the above procedure is obtained 0.51 g of the captioned compound as a pure product.

IR(KBr, cm$^{-1}$): 1785, 1775, 1725, 1665, 1540, 1385.

NMR(100 MHz, d$_6$-DMSO, δ): 2.03 (s, CH$_3$CO), 3.24 & 3.52 (ABq, J=18 Hz, 2-CH$_2$), 3.59 (s, CH$_2$CO), 4.75 & 4.98 (ABq, J=12 Hz, 3-CH$_2$), 4.98 (d, J=4.5 Hz, 6-H), 5.58 (dd, J=4.5 & 8.0 Hz, 7-H), 6.68 (s, thiazolin 5-H), 7.6 (broad s, =NH), 10.68 (d, J=8 Hz, CONH).

EXAMPLE 3

Production of 7-[2-(2-imino-3-hydroxy-4-thiazolin-4-yl)acetamido]-3-acetoxymethyl-3-cephem-4-carboxylic acid In 2 ml of dimethylacetamide is dissolved 0.39 g of 7-(4-chloro-3-oxobutyrylamido)-3-acetoxymethyl-3-cephem-4-carboxylic acid together with 0.07 g of hydroxylamine hydrochloride and 0.082 g of sodium acetate and the solution is allowed to stand at room temperature for 5 hours. To this solution is added 0.1 g of potassium thiocyanate and the mixture is heated at 60° C. for 1 hour. After cooling, 4 ml of ethyl ether is added to this reaction mixture, whereupon an oil separates out. The supernatant fluid is removed by decantation and, with the addition of 10 ml of ethyl acetate to the residue, the vessel wall is rubbed. Thereupon the oil is converted to a powder which is recovered by filtration under suction. By the above procedure is obtained 0.52 g of the captioned compound. Chromatographic analyses of the product show that it is in good agreement with the product obtained in Example 2.

EXAMPLE 4

Production of sodium 7-[2-(2-imino-3-hydroxy-4-thiazolin-4-yl)acetamido]-3-(2-methyl-1,3,4-thiadiazol-5-yl)thiomethyl-3-cephem-4-carboxylate In 20 ml of phosphate buffer (pH 6.4) is dissolved 0.75 g of the 7-[2-(2-imino-3-hydroxy-4-thiazolin-4-yl)acetamido]-3-acetoxymethyl-3-cephem-4-carboxylic acid together with 0.21 g of 2-methyl-1,3,4-thiadiazole-5-thiol and 0.257 g of sodium hydrogen carbonate and the mixed solution is stirred at 57° C. for 15 hours. The solution is adjusted to pH 7.0 with a necessary amount of sodium hydrogen carbonate and subjected to column chromatography on polystyrene resin (Amberlite XAD-2) with water as the developer. The fractions containing the contemplated product are pooled and lyophilized. By the above procedure is obtained the captioned compound. 0.185 g.

IR(cm$^{-1}$, KBr): 1765, 1605, 1550, 1385, 1355.

NMR(100 MHz, D$_2$O, δ): 2.78 (s, thiadiazole 2-CH$_3$), 3.44 & 3.84 (ABq, J=18 Hz, 2-CH$_2$), 3.79 (s, CH$_2$CO), 4.01 & 4.55 (ABq, J=14.0 Hz, 3-CH$_2$), 5.12 (d, J=4.5 Hz, 6-H), 5.72 (d, J=4.5 Hz, 7-H), 6.78 (s, thiazoline 5-H).

Elementary analysis: Calcd. for C$_{16}$H$_{15}$N$_6$O$_5$S$_4$·Na·H$_2$O C; 35.55, H; 3.17, N; 15.55. Found: C; 35.32, H; 3.07, N; 15.46.

| Minimum Inhibitory Concentrations (mcg/ml, agar dilution) | | | |
|---|---|---|---|
| Strain of Bacterium | Present compound | Cephaloridine | Cefazolin |
| E. coli NIHJ | 0.05 | 6.25 | 1.56 |
| E. coli 0-111 | 0.024 | 3.13 | 1.56 |
| E. coli T-7 | 1.56 | >100 | >100 |
| K. pneumoniae DT | 0.05 | 3.13 | 1.56 |
| K. pneumoniae GN 3835 | 0.20 | 50 | 12.5 |
| P. vulgaris IFO 3988 | 0.10 | 6.25 | 3.13 |
| P. mirabilis GN 4359 | 0.05 | 3.13 | 3.13 |
| P. morganii IFO 3168 | 0.10 | >100 | >100 |
| P. rettgeri 8(TNO 336) | 0.012 | 1.56 | 0.20 |
| P. rettgeri GN 4733 | 0.10 | >100 | >100 |
| Ent. cloacae IFO 12937 | 50 | >100 | >100 |
| Cit. freundii GN 99 | 0.78 | 50 | 50 |
| Cit. freundii GN 1706 | 1.56 | >100 | >100 |

EXAMPLE 5

Production of sodium 7-[2-(2-imino-3-hydroxy-4-thiazolin-4-yl)acetamido]-3-(1-methyltetrazol-5-yl)thiomethyl-3-cephem-4-carboxylate A mixed solution of 10 g of 7-(4-bromo-3-oxobutyrylamido)-3-(1-methyltetrazol-5-yl)thiomethyl-3-cephem-4-carboxylic acid and 0.376 g of potassium thiocyanate is stirred at room temperature for 2 hours, at the end of which time 0.14 g of hydroxylamine hydrochloride is added. The mixture is heated to 60° C. and stirred for 1.5 hours. This reaction mixture is stirred with 20 ml of ethyl acetate, whereupon a precipitate is produced. The precipitate is recovered by filtration under suction and dissolved in a solution of 0.5 g sodium hydrogen carbonate in 10 ml of water. The solution is subjected to column chromatography on polystyrene resin (Amberlite XAD-2) with water as the developer. The fractions containing the desired product are pooled and lyophilized. By the above procedure is obtained the captioned compound. Yield 0.345 g.

IR(KBr, cm$^{-1}$): 1765, 1675, 1605, 1390, 1355.

NMR(100 MHz, D$_2$O, δ): 3.47 & 3.83 (ABq, J=18 Hz, 2-CH$_2$), 3.77 (s, CH$_2$CO), 4.07 (s, tetrazole 1-CH$_3$), 4.07 & 4.38 (ABq, J=13 Hz, 3-CH$_2$), 5.12 (d, J=4.5 Hz, 6-H), 5.70 (d, J=4.5 Hz, 7-H), 6.72 (s, thiazoline 5-H).

NMR(100 MHz, d$_6$-DMSO, δ): 3.31 & 3.61 (ABq, J=18 Hz, 2-CH$_2$), 3.56 (s, CH$_2$CO), 3.94 (s, tetrazole 1-CH$_3$), 4.26 & 4.46 (ABq, J=12 Hz, 3-CH$_2$), 4.92 (d, J=4.5 Hz, 6-H), 5.53 (dd, J=4.5 & 8 Hz, 7-H), 6.67 (s, thiazoline 5-H), 10.9 (d, J=8 Hz, CONH).

UVλmax(ε, in H$_2$O): 267 nm(1.325×10$^4$)

Elemental analysis: Calcd. for C$_{15}$H$_{15}$N$_8$O$_5$S$_3$Na·2H$_2$O C; 33.21, H; 3.53, N; 20.65. Found: C; 33.37, H; 3.24, N; 20.49.

| Minimum Inhibitory Concentrations (mcg/ml, agar dilution) | | | |
|---|---|---|---|
| Strain of Bacterium | Present compound | Cephaloridine | Cefazolin |
| E. coli NIHJ | 0.05 | 6.25 | 1.56 |
| E. coli 0-111 | ≦0.03 | 3.13 | 1.56 |
| E. coli T-7 | 1.56 | >100 | >100 |
| K. pneumoniae DT | 0.05 | 3.13 | 1.56 |
| K. pneumoniae GN 3835 | 0.10 | 50 | 12.5 |
| P. vulgaris IFO 3988 | 0.20 | 6.25 | 3.13 |
| P. mirabilis CN 4359 | 0.10 | 3.13 | 3.13 |
| P. morganii IFO 3168 | 0.78 | >100 | >100 |

| Minimum Inhibitory Concentrations (mcg/ml, agar dilution) | | | |
|---|---|---|---|
| Strain of Bacterium | Present compound | Cephaloridine | Cefazolin |
| P. rettgeri 8(TNO 336) | ≦0.03 | 1.56 | 0.20 |
| P. rettgeri GN 4733 | 0.05 | >100 | >100 |
| Ent. cloacae IFO 12937 | 6.25 | >100 | >100 |
| Cit. freundii GN 99 | 0.39 | 50 | 50 |
| Cit. freundii GN 1706 | 0.78 | >100 | >100 |

EXAMPLE 6

Production of sodium 7-[2-(2-imino-3-hydroxy-4-thiazolin-4-yl)acetamido]-3-(5-methyl-1,3,4-oxadiazol-2-yl)thiomethyl-3-cephem-4-carboxylate In 20 ml of phosphate buffer (pH 6.4) is dissolved 1.0 g of 7-[2-(2-imino-3-hydroxy-4-thiazolin-4-yl)acetamido]-3-acetoxymethyl-3-cephem-4-carboxylic acid together with 0.312 g of 5-methyl-1,3,4-oxadiazole-2-thiol potassium salt and 0.336 g of sodium hydrogen carbonate and the mixed solution is stirred at 55° C. for 12 hours. After cooling, this reaction mixture is subjected to column chromatography on polystyrene resin (Amberlite XAD-2) with water as the developer. The fractions containing the contemplated product are pooled and lyophilized. By the above procedure is obtained the captioned compound. Yield 0.21 g.

IR(KBr, cm$^{-1}$): 1770, 1680, 1600, 1485, 1390, 1360
NMR (100 MHz, D$_2$O, β): 2.60 (s, oxadiazole 5-CH$_3$), 3.44 & 3.88 (ABq, J=18 Hz, 2-CH$_2$), 3.78 (s, CH$_2$CO), 3.95 & 4.57 (ABq, J=13 Hz, 3-CH$_2$), 5.12 (d, J=4.5 Hz, 6-H), 5.71 (d, J=4.5 Hz, 7-H), 6.74 (s, thiazoline 5-H).

| Minimum Inhibitory Concentrations (mcg/ml, agar dilution) | | | |
|---|---|---|---|
| Strain of Bacterium | Present compound | Cephaloridine | Cefazolin |
| E. coli NIHJ | 0.10 | 6.25 | 1.56 |
| E. coli 0-111 | 0.05 | 3.13 | 1.56 |
| E. coli T-7 | 3.13 | >100 | >100 |
| K. pneumoniae DT | 0.10 | 3.13 | 1.56 |
| K. pneumoniae GN 3835 | 0.78 | 50 | 12.5 |
| P. vulgaris IFO 3988 | 0.20 | 6.25 | 3.13 |
| P. mirabilis GN 4359 | 0.10 | 3.13 | 3.13 |
| P. morganii IFO 3168 | 0.10 | >100 | >100 |
| P. rettgeri 8(TNO 336) | ≦0.012 | 1.56 | 0.20 |
| P. rettgeri GN 4733 | 0.10 | >100 | >100 |
| Ent. cloacae IFO 12937 | 50 | >100 | >100 |
| Cit. freundii GN 99 | 0.78 | 50 | 50 |
| Cit. freundii GN 1706 | 1.56 | >100 | >100 |

EXAMPLE 7

Production of sodium 7-[2-(2-imino-3-hydroxy-4-thiazolin-4-yl)acetamido]-3-(1H-1,2,3-triazol-4-yl)thiomethyl-3-cephem-4-carboxylate In a 1 N-aqueous solution of sodium hydroxide is dissolved 0.3 g of 5-amino-1,2,3-thiadiazole and the solution is heated at 100° C. for 10 minutes. After cooling, carbon dioxide gas is bubbled into this mixed solution and, after a saturation point is reached, 1.0 g of 7-[2-(2-imino-3-hydroxy-4-thiazolin-4-yl)acetamido]-3-acetoxymethyl-3-cephem-4-carboxylic acid and 20 ml of phosphate buffer (pH 6.4) are added. The mixed solution is heated at 73° C. for 2.5 hours. After cooling, this reaction mixture is subjected to column chromatography on polystyrene resin (Amberlite XAD-2) with water as the developer. The fractions containing the contemplated product are pooled and lyophilized. By the above procedure is obtained the captioned compound. Yield 0.285 g.

IR(KBr, cm$^{-1}$): 1770, 1610, 1400, 1360.
NMR(100 MHz, D$_2$O, δ): 3.33 & 3.78 (ABq, J=18 Hz, 2-CH$_2$), 3.75 (s, CH$_2$CO), 3.63 & 4.22 (ABq, J=4.0 Hz, 3-CH$_2$), 5.06 (d, J=4.0 Hz, 6-H), 5.62 (d, J=4.0 Hz, 7-H), 6.70 (s, thiazoline 5-H), 7.94 (s, triazole 5-H).

Elemental analysis: Calcd. for C$_{15}$H$_{14}$N$_7$O$_5$S$_3$Na.0.5-H$_2$O C; 36.00, H; 3.02, N; 19.59. Found: C; 35.65; H; 3.51, N; 19.67.

| Minimum Inhibitory Concentrations (mcg/ml, agar dilution) | | | |
|---|---|---|---|
| Strain of Bacterium | Present compound | Cephaloridine | Cefazolin |
| E. coli NIHJ | 0.78 | 6.25 | 1.56 |
| E. coli 0-111 | 0.05 | 3.13 | 1.56 |
| E. coli T-7 | 3.13 | >100 | >100 |
| K. pneumoniae DT | 0.10 | 3.13 | 1.56 |
| K. pneumoniae GN 3835 | 0.10 | 50 | 12.5 |
| P. vulgaris IFO 3988 | 0.20 | 6.25 | 3.13 |
| P. mirabilis GN 4359 | 0.10 | 3.13 | 3.13 |
| P. morganii IFO 3168 | 0.39 | >100 | >100 |
| P. rettgeri 8(TNO 336) | ≦0.03 | 1.56 | 0.20 |
| P. rettgeri GN 4733 | 0.78 | >100 | >100 |
| Ent. cloacae IFO 12937 | >100 | >100 | >100 |
| Cit. freundii GN 99 | 1.56 | 50 | 50 |
| Cit. freundii GN 1706 | 12.5 | >100 | >100 |

EXAMPLE 8

Production of sodium 7-[2-(2-imino-3-hydroxy-4-thiazolin-4-yl)acetamido]-3-(3-hydroxymethyl-4-methyl-1,2,4-triazol-5-yl)thiomethyl-3-cephem-4-carboxylate In 20 ml of phosphate buffer (pH 6.4) is dissolved 1.0 g of 7-[2-(2-imino-3-hydroxy-4-thiazolin-4-yl)acetamido]-3-acetoxymethyl-3-cephem-4-carboxylic acid together with 0.3 g of 3-hydroxymethyl-4-methyl-1,2,4-triazole-5-thiol and 0.336 g of sodium hydrogen carbonate and the solution is stirred at 70° C. for 2 hours. This reaction mixture is subjected to column chromatography on polystyrene resin (Amberlite XAD-2) with water as the developer and the fractions containing the contemplated product are pooled. This solution contains 3-hydroxymethyl-4-methyl-1,2,4-triazole-5-thiol together with the desired compound. The solution is lyophilized and the resultant powder is redissolved in water. The solution is then subjected to column chromatography on dextran gel (Sephadex LH-20 ®, Pharmacia) with water as the developer. The fractions containing the contemplated compound are pooled and lyophilized. By the above procedure is obtained the captioned compound. Yield 0.28 g.

IR(KBr, cm$^{-1}$): 1770, 1675, 1605, 1390, 1360
NMR(100 MHz, D$_2$O, δ): 3.39 & 3.85 (ABq, J=18 Hz, 2-CH$_2$), 3.74 (s, triazole 4-CH$_3$), 3.77 (s, CH$_2$CO), 3.76 & 4.35 (ABq, J=14 Hz, 3-CH$_2$), 4.81 (s, triazole 3-CH$_2$OH), 5.08 (d, J=4.5 Hz, 6-H), 5.66 (d, J=4.5 Hz, 7-H), 6.73 (s, triazoline 5-H).

| Minimum Inhibitory Concentrations (mcg/ml, agar dilution) | | | |
|---|---|---|---|
| Strain of Bacterium | Present compound | Cephaloridine | Cefazolin |
| E. coli NIHJ | ≦0.2 | 6.25 | 1.56 |
| E. coli 0-111 | ≦0.2 | 3.13 | 1.56 |
| E. coli T-7 | 1.56 | >100 | >100 |
| K. pneumoniae DT | ≦0.2 | 3.13 | 1.56 |

-continued

| Minimum Inhibitory Concentrations (mcg/ml, agar dilution) | | | |
|---|---|---|---|
| Strain of Bacterium | Present compound | Cephaloridine | Cefazolin |
| K. pneumoniae GN 3835 | ≦0.2 | 50 | 12.5 |
| P. vulgaris IFO 3988 | 0.39 | 6.25 | 3.13 |
| P. mirabilis GN 4359 | ≦0.2 | 3.13 | 3.13 |
| P. morganii IFO 3168 | ≦0.2 | >100 | >100 |
| P. rettgeri 8 (TNO 336) | ≦0.2 | 1.56 | ≦0.2 |
| P. rettgeri GN 4733 | ≦0.2 | >100 | >100 |
| Ent. cloacae IFO 12937 | 12.5 | >100 | >100 |
| Cit. freundii GN 99 | 0.78 | 50 | 50 |
| Cit. freundii GN 1706 | 3.13 | >100 | >100 |

EXAMPLE 9

Production of 7-[2-(2-imino-3-hydroxy-4-thiazolin-4-yl)acetamido]-3-(1-methyltetrazol-5-yl)thiomethyl-3-cephem-4-carboxylic acid In 10 ml of dimethylacetamide is dissolved 4.0 g of 7-(4-bromo-3-oxobutyrylamido)-3-(1-methyltetrazol-5-yl) thiomethyl-3-cephem-4-carboxylic acid together with 1.5 g of potassium thiocyanate and 0.56 g of hydroxylamine hydrochloride and the solution is stirred at 60° C. for 60 minutes. After cooling, the reaction mixture is mixed with 40 ml of ethyl ether, whereupon an oil separates out. The supernatant fluid is discarded by decantation and with the addition of 100 ml of ethyl acetate to the residue, the vessel wall is rubbed, whereupon the oil turns into a powder. This powder is recovered by filtration under suction (5.2 g) and dissolved in 25 ml of an aqueous solution of 2.2 g of sodium hydrogen carbonate. The solution is column-chromatographed on polystyrene resin (Amberlite XAD-2) with water as the developer. The fractions containing the desired compound are pooled and concentrated to 10 ml under reduced pressure. The concentrate is adjusted to pH 3 with acetic acid and further concentrated to 5 ml under reduced pressure. The concentrate is allowed to stand and the resultant crystals are collected by filtration and recrystallized from water. By the above procedure is obtained the captioned compound.

m.p. 200°–220° C. (decomp.).

IR(KBr, cm$^{-1}$): 1785, 1660, 1630, 1550, 1385.

NMR(100 MHz, CF$_3$COOH, δ): 3.87 (s, 2-CH$_2$), 4.10 (s, CH$_2$CO), 4.21 (s, tetrazole 1-CH$_3$), 4.23 & 4.76 (ABq, J=14 Hz, 3-CH$_2$), 5.27 (d, J=4.5 Hz, 6-H), 5.88 (dd, J=4.5 & 8.0 Hz, 7-H), 6.81 (s, thiazoline 5-H), 8.09 (d, J=8.0 Hz, CONH).

Elemental analysis: Calcd. for C$_{15}$H$_{16}$N$_8$O$_5$S$_3$·½H$_2$O C; 36.50, H; 3.47, N; 22.70. Found: C; 36.68; H; 3.37, N; 22.71.

Toxicology tests

Subcutaneous dose of up to 1 g/kg of the compound obtained by Example 9 on mice and rats have revealed no adverse effects.

EXAMPLE 10

Production of 7-[2-(2-imino-3-hydroxy-4-thiazolin-4-yl)acetamido]-3-(4-carbamoylpyridinium)methyl-3-cephem-4-carboxylic acid betain In 40 ml of phosphate buffer (pH 6.4) is dissolved 2.0 g of 7-[2-(2-imino-3-hydroxy-4-thiazolin-4-yl)acetamido]-3-acetoxymethyl-3-cephem-4-carboxylic acid together with 1 g of isonicotinamide, 4.0 g of sodium iodide and 0.164 g of sodium hydrogen carbonate and the solution is stirred at 50° C. for 15 hours. After cooling, the reaction mixture was column-chromatographed on polystyrene resin (Amberlite XAD-2) with water as the developer. The fractions containing the contemplated product are pooled and lyophilized. By the above procedure is obtained the captioned compound. Yield 0.254 g.

IR(KBr, cm$^{-1}$): 1775, 1690, 1620, 1395, 1360.

NMR(100 MHz, D$_2$O, δ): 3.21 & 3.70 (ABq, J=18 Hz, 2-CH$_2$), 3.74 (s, CH$_2$CO), 5.21 (d, J=4.0 Hz, 6-H), 5.43 & 5.69 (ABq, J=14 Hz, 3-CH$_2$), 5.75 (d, J=4 Hz, 7-H), 6.72 (s, thiazoline 5-H), 8.40 & 9.15 (each d, J=6 Hz, pyridine α & β-H).

| Minimum Inhibitory Concentrations (mcg/ml, agar dilution) | | | |
|---|---|---|---|
| Strain of Bacterium | Present compound | Cephaloridine | Cefazolin |
| E. coli NIHJ | 1.56 | 6.25 | 1.56 |
| E. coli 0-111 | 0.39 | 3.13 | 1.56 |
| E. coli T-7 | 25 | >100 | >100 |
| K. pneumoniae DT | 0.78 | 3.13 | 1.56 |
| K. pneumoniae GN 3835 | 1.56 | 50 | 12.5 |
| P. vulgaris IFO 3988 | 0.78 | 6.25 | 3.13 |
| P. mirabilis GN 4359 | 0.78 | 3.13 | 3.13 |
| P. morganii IFO 3168 | 3.13 | >100 | >100 |
| P. rettgeri 8(TNO 336) | ≦0.2 | 1.56 | ≦0.2 |
| P. rettgeri GN 4733 | ≦0.2 | >100 | >100 |
| Ent. cloacae IFO 12937 | 25 | >100 | >100 |
| Cit. freundii GN 99 | 1.56 | 50 | 50 |
| Cit. freundii GN 1706 | 12.5 | >100 | >100 |

EXAMPLE 11

Production of 7-[2-(2-amino-3-hydroxy-4-thiazolin-4-yl)acetamido]-3-(mandeloxymethyl-3-cephem-4-carboxylic acid.

In 10 ml of dimethtylacetamide is dissolved 5.3 g of 7-(4-bromo-3-oxobutyrylamido)-3-(mandeloxymethyl)-3-cephem-4-carboxylic acid together with 1.0 g of potassium thiocyanate and the solution is allowed to stand at room temperature for 15 hours. To this mixed solution is added 0.7 g of hydroxylamine hydrochloride and the mixture is heated at 60° C. for 2 hours. After cooling, 40 ml of ethyl ether is added to the reaction mixture, whereupon an oil separates. The supernatant fluid is discarded by decantation and, with the addition of 100 ml of ethyl ether, the vessel wall is rubbed. The resultant powder is recovered by filtration. The above procedure yields 5.8 g of the captioned compound as a crude powder. A 1 g-portion of this powder is taken and dissolved in 50 ml of a 10% aqueous solution of sodium hydrogen carbonate and filtered under suction. The filtrate is adjusted to pH 3 with acetic acid and concentrated to about 2 ml under reduced pressure. The concentrate is allowed to stand in a refrigerator and the resultant crystalline powder is collected by filtration and dried. By the above procedure is obtained 0.62 g of the captioned compound as a pure product.

IR(KBr, cm$^{-1}$): 1776

NMR(100 MHz, d$_6$-DMSO-D$_2$O, δ): 3.30 & 3.61 (ABq, J=18 Hz, 2-CH$_2$), 3.45 (s, CH$_2$CO), 4.8–5.4 (m, 2H, 3-CH$_2$), 4.90 (d, J=5 Hz, 6-H), 5.20 (s, Ph-CH(OH)-), 5.52 (d, J=5 Hz, 7-H), 6.68 (s, thiazolin 5-H), 7.2–7.6 (m, 5H, C$_6$H$_5$-)

EXAMPLE 12

Production of
7-[2-(2-imino-3-hydroxy-4-thiazolin-4-yl)acetamido]-3-nitrogen-containing heterocyclic thiomethyl-3-cephem-4-carboxylic acid [I]-betain or -sodium salt.

In accordance with the general production procedures described below, 7-[2-(2-imino-3-hydroxy-4-thiazolin-4-yl) acetamido]-3-acetoxymethyl-3-cephem-4-carboxylic acid or 7-[2-(2-imino-3-hydroxy-4-thiazolin-4-yl)acetamido]-3-hydroxy-4-thiazolin-4-yl)acetamido]-3-mandeloxymethyl-3-cephem-4-carboxylic acid is reacted with the corresponding nitrogen-containing heterocyclic thiol to produce the compounds No. 1 to No. 34 listed in the table hereinafter. The physical properties of the compounds are also shown.

General production procedure (1)

In 40 ml of phosphate buffer (pH 6.4) is dissolved 0.856 g (2 millimoles) of 7-[2-(2-imino-3-hydroxy-4-thiazolin-4-yl)acetamido]-3-acetoxymethyl-3-cephem-4-carboxylic acid together with the nitrogen-containing heterocyclic thiol (2.2 millimoles) and 0.336 g (4 millimoles) of sodium hydrogen carbonate and the mixed solution is stirred at 70°-65° C. for 7-8 hours. The reaction mixture is concentrated under reduced pressure to about 20 ml and, after adjusting the pH of the concentrate to 6.5 with 10% sodium hydrogen carbonate or 10% phosphoric acid, as whichever is required, subjected to column chromatography on polystyrene resin (Amberlite XAD-2). Elution is carried out with water, 5% ethanol and 10% ethanol in the order mentioned. The fractions containing the desired product are pooled and the alcohol is distilled off under reduced pressure. The residue is lyophilized. By the above procedure is obtained 7-[2-(2-imino-3-hydroxy-4-thiazolin-4-yl)acetamido]-3-nitrogen-containing heterocyclic thiomethyl-3-cephem-4-carboxylic acid betain or sodium.

General production procedure (2)

In 15 ml of water is dissolved 1 g (2 millimoles) of 7-[2-(2-imino-3-hydroxy-4-thiazolin-4-yl)acetamido]-3-(mandeloxymethyl)-3-cephem-4-carboxylic acid together with the nitrogen-containing heterocyclic thiol (2 millimoles) and 0.25 g (3 millimoles) of sodium hydrogen carbonate and the mixed solution is stirred t 60° C. for 1 hour. After cooling, the solution is adjusted to pH 6 with 10% sodium hydrogen carbonate and subjected to column chromatography on dextran gel (Sephadex LH-20) with water as the developer. The fractions containing the contemplated product are pooled and lyophilized. By the above procedure is obtained the captioned compound 7-[2-(2-imino-3-hydroxy-4-thiazolin-4-yl) acetamido]-3-nitrogen-containing heterocyclic thiomethyl-3-cephem-4-carboxylic acid betaine or sodium.

General production procedure (3):

(1) In 40 ml of water is dissolved 10.7 g (30 millimoles) of 7-acetoacetamido-3-acetoxymethyl-3-cephem-4-carboxylic acid together with the nitrogen-containing heterocyclic thiol (30 millimoles) and 5.04 g (60 millimoles) of sodium hydrogen carbonate. The solution is adjusted to pH 7.0 with 10% sodium hydroxide and stirred at 60°-65° C. for 4 hours. After cooling, 2.31 g (33 millimoles) of hydroxylamine hydrochloride is added and the mixture is adjusted to pH 3.6 with a necessary amount of 1 N-hydrochloric acid. The mixture is allowed to stand at room temperature overnight. The resultant crystals are recovered by filtration, washed with acetone and dried. By the above procedure is obtained the desired 7-amino-3-nitrogen-containing heterocyclic thiomethyl-3-cephem-4-carboxylic acid.

(2) A solution of 1.03 g (13 millimoles) of diketene in 5 ml of methylene chloride is cooled to −30° C. and 15 g (15 millimoles) of a solution of 1 mole of chlorine (by weight) in carbon tetrachloride or a solution of 2.24 g (14 millimoles) of bromine in 5 ml of methylene chloride is added dropwise. Separately, the 7-amino-3-nitrogen-containing heterocyclic thiomethyl-3-cephem-4-carboxylic acid (10 millimoles) and 2.02 g (20 millimoles) of triethylamine are dissolved in 20 ml of methylene chloride and the solution is cooled to −20° C. To this solution is added the above reaction mixture dropwise and in a quick manner. In most cases this dropwise addition results in the evolution of heat, increasing the temperature to near 0° C. The temperature of the mixture is gradually increased to room temperature, at which level the mixture is stirred for 15 minutes. The reaction mixture is added to a mixture of 150 ml ethyl acetate and 100 ml of 10% phosphoric acid and stirred intensely. The organic layer is separated, washed with water, dried and concentrated to dryness. The residue is loosened with ether. By the above procedure is obtained 7-(4-chloro(where chlorine is employed)- or bromo (where bromine is employed)-3-oxobutyrylamido)-3-nitrogen-containing heterocyclic thiomethyl-3-cephem-4-carboxylic acid as a powder.

(3) In 10 ml of dimethylacetamide is dissolved 7-(4-chloro- or bromo-3-oxobutyrylamido)-3-nitrogen-containing heterocyclic thiomethyl-3-cephem-4-carboxylic acid (8 millimoles) and 0.776 g (8 millimoles) of potassium thiocyanate and the mixed solution is allowed to stand at room temperature for 12 hours. To this reaction mixture is added 0.56 g (8 millimoles) of hydroxylamine hydrochloride and the mixture is stirred at 60° C. for 60 minutes. After cooling, the reaction mixture is stirred with 40 ml of ethyl ether and the supernatant fluid is removed by decantation. With the addition of 100 ml of ethyl acetate, the vessel wall is rubbed. The resultant powder is recovered by filtration under suction and dissolved in 20 ml of 10% sodium hydrogen carbonate. The solution is subjected to column chromatography on polystyrene resin (Amberlite XAD-2) with water as the developer. The fractitons containing the contemplated product are pooled and lyophilized. By the above procedure is obtained the captioned compound 7-[2-(2-imino-3-hydroxy-4-thiazolin-4-yl)acetamido]-3-nitrogen-containing heterocyclic thiomethyl-3-cephem-4-carboxylic acid betain or sodium.

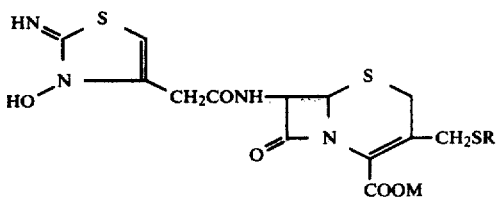

| Compound No. | R | IR M β-lactam (KBr)cm$^{-1}$ | NMR, δppm | General production procedure |
|---|---|---|---|---|
| 1 | (2-methyl-thiazol-4-yl with CH₃) | Na 1765 | (100MHz, D₂O): 2.55(s, thiazole 5-CH₃), 3.44 & 3.86(ABq,J = 18Hz, 2-CH₂), 3.85(s,CH₂CO), 3.91 & 4.58(ABq,J = 14Hz, 3-CH₂), 5.15(d,J = 4.5Hz, 6-H), 5.73(d,J = 4.5Hz, 7-H), 6.79(s,thiazoline 5-H), 7.52(s,thiazole 4-H) | (1) (2) (3) |
| 2 | (thiazolyl-CH₂COONa) | Na 1767 | (100MHz, D₂O): 3.43 & 3.83(ABq,J = 18Hz,2-CH₂), 3.76(s,CH₂CO), 3.84(s, CH₂CO), 4.01 & 4.59 (ABq,J = 14Hz,3-CH₂), 5.15(d,J = 5Hz,6-H), 5.72 (d,J = 5Hz,7-H), 6.79(s, thiazoline 5-H), 7.36 (s,thiazole 5-H) | (1) (2) |
| 3 | (triazolyl NH) | Na 1768 | (100MHz, D₂O): 3.46 & 3.79(ABq,J = 18Hz,2-CH₂), 3.77(s,CH₂CO), 4.04 & 4.28(ABq, J = 14Hz,3-CH₂), 5.12(d,J = 5Hz,6-H), 5.68 (d,J = 5Hz,7-H), 6.73(s, thiazoline 5-H), 8.36 (s,triazole 5-H) | (1) (2) (3) |
| 4 | (dimethyl triazolyl) | Na 1765 | (100MHz, D₂O): 2.53(s, triazole 5-CH₃), 3.44 & 4.01(ABq,J = 18Hz,2-CH₂), 3.68(s,triazole 4-CH₃), 3.85(s,CH₂CO), 3.75 & 4.42(ABq,J = 14Hz,3-CH₂), 5.14(d,J = 4Hz,6-H), 5.70 (d,J = 4Hz,7-H), 6.73(s, thiazoline 5-H) | (1) (2) (3) |
| 5 | (methyl imidazolyl) | Na 1766 | (100MHz, D₂O): 3.33 & 3.86(ABq,J = 18Hz,2-CH₂), 3.83(s,CH₂CO & 1,3-diazole-CH₃), 5.13(d, J = 5Hz,6-H), 5.69(d, J = 5Hz,7-H), 6.74(s,thiazoline 5-H), 7.14 & 7.30 (each d,J = 1Hz,1,3-diazole 4- & 5-H) | (1) (2) (3) |
| 6 | (N-methyl triazolyl) | Na 1765 | (100MHz, D₂O): 3.48 & 3.90(ABq,J = 18Hz,2-CH₂), 3.81(s,CH₂CO), 4.00 & 4.45(ABq,J = 13Hz,3-CH₂), 5.19(d,J = 5Hz,6-H), 5.75 (d,J = 5Hz,7-H), 6.74(s, thiazoline 5-H), 8.11 (s, 1,2,4-triazole 3-H) | (1) (2) (3) |
| 7 | (thiadiazolyl) | Na 1765 | (100MHz, D₂O): 3.43 & 3.78(ABq,J = 18Hz,2-CH₂), 3.77(s,CH₂CO) 4.09 & 4.54(ABq,J = 13Hz,3-CH₂), 5.09(d,J = 5Hz,6-H), 5.65 (d,J = 5Hz,7-H), 6.73(s, thiazoline 5-H) | |

-continued

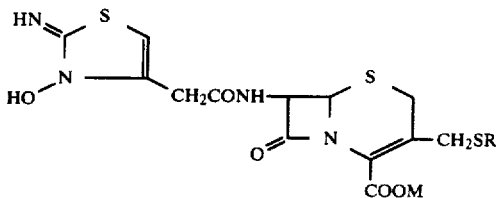

| Compound No. | R | IR M β-lactam (KBr)cm⁻¹ | NMR, δppm | General production procedure |
|---|---|---|---|---|
| 8 | N—N, triazole with N-CH₃ | Na 1767 | (100MHz, D₂O): 3.48 & 3.90(ABq,J = 18Hz,2-CH₂), 3.82(s,CH₂CO & triazole-CH₃), 3.83 & 4.38(ABq, J = 14Hz,3-CH₂), 5.15(d, J = 5Hz,6-H), 5.70(d, J = 5Hz,7-H), 6.75(s, thiazoline 5-H), 8.59 (s,triazole 5-H) | (1) (2) (3) |
| 9 | N—N, S, NH₂ | Na 1768 | (100MHz, D₂O): 3.45 & 3.89(ABq,J = 18Hz,2-CH₂), 3.85(s,CH₂CO), 3.90 & 4.52(ABq,J = 13Hz,3-CH₂), 5.19(d,J = 5Hz,6-H), 5.76 (d,J = 5Hz,7-H), 6.74(s, thiazoline 5-H) | (1) (2) (3) |
| 10 | N—N, S, NHCOOCH₃ | Na 1765 | (100MHz, D₂O): 3.48 & 3.90(ABq,J = 18Hz,2-CH₂), 3.86(s,CH₂CO), 3.89(s, OCH₃), 3.90 & 4.51(ABq, J = 13Hz,8-CH₂), 5.19(d, J = 5Hz,6-H), 5.76(d, J = 5Hz,7-H), 6.75(s, thiazoline 5-H) | (1) (2) (3) |
| 11 | N—N, S, CH₂CON(CH₃)₂ | Na 1765 | (100MHz, D₂O): 3.13 & 3.29(each s, N(CH₃)₂), 3.55 & 3.89(ABq,J = 18Hz, 2-CH₂), 3.87(s,CH₂CO), 4.21 & 4.62(ABq,J = 14Hz, 3-CH₂), 5.22(d,J = 5Hz, 6-H), 5.78(d,J = 5Hz, 7-H), 6.75(s,thiazoline 5-H) | (1) (2) (3) |
| 12 | N—N, S, CH₂COONa | Na 1767 | (100MHz, D₂O): 3.56 & 3.92(ABq,J = 18Hz,CH₂), 3.81(s,CH₂CO), 4.17(s, CH₂CO₂), 4.20 & 4.62 (ABq,J = 13Hz,3-CH₂), 5.24(d,J = 5Hz,6-H), 5.80(d,J = 5Hz,7-H), 6.73(s,thiazoline 5-H) | (1) (2) |
| 13 | N—N, S, CH₂COOCH₃ | Na 1768 | (100MHz, D₂O): 3.53 & 3.88(ABq,J = 18Hz,2-CH₂), 3.86(s,CH₂CO), 3.91(s, OCH₃), 4.18 & 4.58(ABq, J = 13Hz,3-CH₂), 5.21(d, J = 5Hz,6-H), 5.77(d, J = 5Hz,7-H), 6.73(s, thiazoline 5-H) | (2) |
| 14 | N—N, S, CH₂CONH₂ | Na 1770 | (100MHz, D₂O): 3.52 & 3.87(ABq,J = 18Hz,2-CH₂), 3.86(s,CH₂CO), 4.18 & 4.57(ABq,J = 13Hz,3-CH₂), 5.19(d,J = 5Hz,6-H), 5.75 (d,J = 5Hz,7-H), 6.73(s, thiazoline 5-H) | (1) (2) (3) |
| 15 | N—N, S, CH₂SCH₃ | Na 1765 | (100MHz, D₂O): 2.25(s, CH₃S), 3.54 & 3.86(ABq, J = 18Hz,2-CH₂), 3.86(s, CH₂CO), 4.22(s,CH₂S), 4.25 & 4.59(ABq,J = 14Hz, 3-CH₂), 5.20(d,J = 5Hz, 6-H), 5.79(d,J = 5Hz,7-H), 6.75(s,thiazoline 5-H) | (1) (2) (3) |

-continued

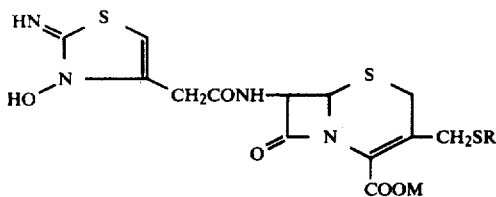

| Compound No. | R | IR M β-lactam (KBr)cm$^{-1}$ | NMR, δppm | General production procedure |
|---|---|---|---|---|
| 16 | N——N, ⫩_S⫩CH₂OCH₃ | | (100MHz, D₂O): 3.36(s, OCH₃), 3.30 & 3.64(ABq, J = 18Hz,2-CH₂), 3.63(s, CH₂CO), 3.97 & 4.38 (ABq, J = 14Hz,3-CH₂), 4.77(s,CH₂O), 4.96(d, J = 5Hz,6-H), 5.52(d, J = 5Hz,7-H), 6.74(s, thiazoline 5-H) | (1) (2) (3) |
| 17 | N——N, ⫩_S⫩SCH₂COONa | Na 1765 | (100MHz, D₂O): 3.37 & 3.77(ABq,J = 17Hz,2-CH₂), 3.76(s,CH₂CON), 3.97 & 4.40(ABq, J = 14Hz,3-CH₂), 5.08(d,J = 5Hz,6-H), 5.64 (d,J = 5Hz,7-H), 6.71(s, thiazoline 5-H) | (2) |
| 18 | N——N, ⫩_S⫩SCH₂CH₂OH | Na 1768 | (100MHz, D₂O): 3.4-3.8(m, s × CH₂), 3.97(t,J = 6Hz, CH₂O), 4.01 & 4.42(ABq, J = 14Hz,3-CH₂), 5.06(d, J = 5Hz,6-H), 5.64(d, J = 5Hz,7-H), 6.75(s, thiazoline 5-H) | (1) (2) (3) |
| 19 | N——N, ⫩_N⫩CH₂CH₂N(CH₃)₂ ⊕ | ⊖ 1768 | (100MHz, D₂O): 3.02(s, N(CH₃)₂), 3.48 & 3.78 (ABq,J=18Hz,2-CH₂), 3.75(s,CH₂CO), 3.79(t, J=6Hz,CH₂NMe₂), 4.12 & 4.29(ABq,J=13Hz,3-CH₂), 4.83(t,J=6Hz,tetrazole-CH₂—), 5.10(d,J=5Hz,6-H), 5.61(d,J=5Hz,7-H), 6.72 (s,thiazoline 5-H) | (2) |
| 20 | N——N, ⫩_N⫩CH₂CONH₂ | Na 1767 | (100MHz, D₂O): 3.53 & 3.85(ABq,J=18Hz,2-CH₂), 3.85(s,CH₂CO), 4.25 & 4.49(ABq,J=13Hz,3-CH₂), 5.21(d,J=5Hz,6-H), 5.42 (s,NCH₂CO), 5.76(d, J=5Hz,7-H), 6.74(s, thiazoline 5-H) | (1) (2) (3) |
| 21 | N——N, ⫩_S⫩CH₂NHCNH₂ ‖ NH | H 1770 | (100MHz, CF₃COOH): 3.79 (s,2-CH₂), 4.12(s,CH₂CO), 4.40 & 4.81(ABq,J=14Hz, 3-CH₂), 5.12(d,J=7Hz, thiadiazole-CH₂—), 5.27 (d,J=4.5Hz,6-H), 5.88 (dd,J=4.5 & 8Hz,7-H), 6.4-7.0(broad,5H,—NHC (=NH)NH₂ & thiazoline 5-H) | (1) |
| 22 | N——N, ⫩_N⫩CH₂COONa | Na 1765 | (100MHz, D₂O): 3.44 & 3.68(ABq,J=18Hz,2-CH₂), 3.72(s,CH₂CO), 4.23 & 4.42(ABq,J=13Hz,3-CH₂), 4.71(s,tetrazole-CH₂CO), 4.96(d,J=5Hz,6-H), 5.58 (d,J=5Hz,7-H), 6.73(s, thiazoline 5-H) | (1) |

-continued

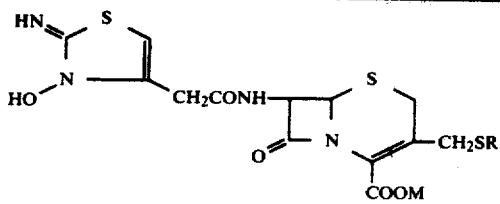

| Compound No. | R | IR M β-lactam (KBr)cm$^{-1}$ | NMR, δppm | General production procedure |
|---|---|---|---|---|
| 23 | N—N with CH₃ groups, N-Na | Na 1765 | (100NHz, D₂O): 3.42 & 3.80(ABq,J=18Hz,2-CH₂), 3.73(s,CH₂CO), 3.99 & 4.36(ABq,J=13Hz,3-CH₂), 5.16(d,J=5Hz,6-H), 5.74 (d,J=5Hz,7-H), 6.80(s, thiazoline 5-H) | (1) |
| 24 | N—N, S, CH₂OH | Na 1772 | (100MHz, D₂O): 3.44 & 3.85(ABq,J=18Hz,2-CH₂), 3.79(s,CH₂CO), 4.08 & 4.58(ABq,J=13Hz,3-CH₂), 5.01(s,thiadiazol-CH₂O), 5.12(d,J=4.5Hz,6-H), 5.71(d,J=4.5Hz,7-H), 6.74(s,thiazoline 5-H) | (1) (2) (3) |
| 25 | N—N, S, CH₂N(CH₃)₂ | Na 1767 | (100MHz, D₂O): 2.51(s, N(CH₃)₂), 3.77(s,CH₂CO), 3.44 & 3.79(ABq,J=18Hz, 2-CH₂), 4.12 & 4.53(ABq, J=13Hz,3-CH₂), 4.22(s, thiadiazol-CH₂N), 5.10 (d,J=5Hz,6-H), 5.66(d, J=5Hz,7-H), 6.70(s, thiazoline 5-H) | (2) |
| 26 | N—N, S, SCH₂CH₂SO₃Na | Na 1768 | (100MHz, D₂O): 3.0–3.8 (m, 8H), 4.02 & 4.27 (ABq,J=13Hz,3-CH₂), 5.04(d,J=5Hz,6-H), 5.58 (d,J=5Hz,7-H), 6.75(s, thiazoline 5-H) | (1) |
| 27 | N—N, N, CH₂OCH₃ | Na 1768 | (100MHz, D₂): 3.46(s, OCH₃), 3.47 & 3.82(ABq, J=18Hz,2-CH₂), 3.77(s, CH₂CO), 4.18 & 4.45(ABq, J=13Hz,3-CH₂), 5.12(d, J=4.5Hz,6-H), 5.67(d, J=4.5Hz, 7-H), 5.77(s, tetrazole-CH₂O), 6.73 (s, thiazoline 5-H) | (1) (2) (3) |
| 28 | N—N, N, CH₂SCH₃ | Na 1767 | (100MHz, D₂O): 2.21(s, SCH₃), 3.45 & 3.78(ABq, J=18Hz,2-CH₂), 3.77(ABq, CH₂CO), 4.20 & 4.44(ABq, J=13Hz,3-CH₂), 5.12(d, J=5Hz,6-H), 5.46(s, tetrazole-CH₂S), 5.68(d, J=5Hz,7-H), 6.72(s, thiazoline 5-H) | (1) (2) (3) |
| 29 | N—N, S, CH₂CH₂OH | Na 1709 | (100MHz, D₂O): 2.93(t, J=6Hz,thiadiazole 2-CH₂), 3.4–3.9(m,6H), 4.03 & 4.56(ABq,J=14Hz,3-CH₂), 5.12(d,J=4.5Hz,6-H), 5.73(d,J=4.5Hz,7-H), 6.74 (s, thiazoline 5-H) | (1) (2) (3) |
| 30 | N—N, N, CH₂CH₂NH₃⁺ | ⊖ 1770 | (100MHz, D₂O + NaHCO₃): 3.45–3.78(m,6H,2-CH₂, CH₂CO & CH₂ NH₂), 4.23 & 4.45(ABq,J=13Hz,3-CH₂), 4.6–4.8(m,tetrazole-CH₂), 5.15(d,J=4.5Hz, 6-H), 5.73(d,J-4.5Hz,7-H), 6.73 (s, thiazoline 5-H) | (2) |

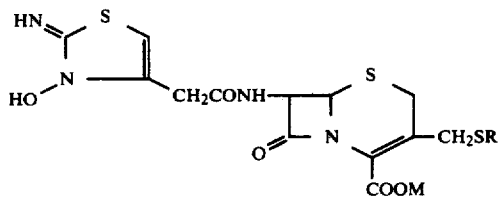

| Compound No. | R | IR M β-lactam (KBr)cm⁻¹ | NMR, δppm | General production procedure |
|---|---|---|---|---|
| 31 | ![N-N triazole with N-CH3 and CH2COONa] | Na 1765 | (100MHz, D₂O): 3.45 & 4.03(ABq,J=18Hz,2-CH₂), 3.62(s,triazole 4-CH₂), 3.78(s,triazole 5-CH₂CO), 3.85(s,CH₂CO), 3.75 & 4.43(ABq,J=14Hz,3-CH₂), 5.14(d,J=4Hz,6-H), 5.71 (d,J=4Hz,7-H), 6.73(s, thiazoline 5-H) | (1) |
| 32 | ![N-N thiadiazole with CH2CH2N(CH3)2] | Na 1768 | (100MHz, D₂O): 3.02(s, (CH₃)₂N), 3.46 & 3.84 (ABq,J=18Hz,2-CH₂), 3.67(broad s,CH₂CH₂N), 3.78(s,CH₂CO), 4.06 & 4.53(ABq,J=14Hz,3-CH₂), 5.16(d,J=5Hz,6-H), 5.71 (d,J=5Hz,7-H), 6.75(s, thiazoline 5-H) | (2) |
| 33 | ![tetrazole with CH2CH2NHCOCH3] | Na 1760 | (100MHz, D₂O): 2.03(s, COCH₃), 3.54 & 3.87(ABq, J=18Hz,2-CH₂), 3.84(s, CH₂CO), 4.22 & 4.48(ABq, J=13Hz,3-CH₂), 3.7–3.9 & 4.5–4.8(each m, CH₂CH₂), 5.20(d,J=4.5Hz,6-H), 5.77 (d,J=4.5Hz,7-H), 6.80(s, thiazoline 5-H) | (1) (2) (3) |
| 34 | ![tetrazole with CH2CH2NHCH3⊕ and NCH3] | ⊖ 1768 | (100MHz, D₂O): 2.96 (s,NCH₃), 3.63 & 3.93(ABq, J=18Hz,2-CH₂), 3.83(t, J=6Hz, CH₂NMe), 3.82(s, CH₂CO), 4.23 & 4.44(ABq, J=14Hz,3-CH₂), 4.94(t, J=6Hz,tetrazole-CH₂—), 5.24(d,J=5Hz,6-H), 5.75 (d,J=5Hz,7-H), 6.81(s, thiazoline 5-H) | |

EXAMPLE 13

Production of sodium 7-[2-(2-imino-3-hydroxy-4-thiazolin-4-yl)acetamido]-3-(carbamoyloxymethyl)-3-cephem-4-carboxylate In 0.5 ml of dimethylacetamide is dissolved 0.088 g of 7-(4-bromo-3-oxobutyrylamido)-3-(carbamoyloxymethyl)-3-cephem-4-carboxylic acid together with 0.019 g of potassium thiocyanate and the resultant solution is stirred at room temperature for 1 hour. To this solution is added 0.014 g of hydroxylamine hydrochloride and the obtained solution is heated at 50° C. and stirred for 1 hour. To this reaction mixture is added 10 ml of ether and the supernatant fluid is removed by decantation. With the addition of 10 ml of ether, the residue is stirred, whereupon a powder is obtained. This powder is recovered by filtration under suction and dissolved in a 10% aqueous solution of sodium hydrogen carbonate. The solution is subjected to column chromatography of polystyrene resin (Amberlite XAD-2) with water as the developer. The fractions containing the captioned product are pooled and lyophilized. By the above procedure is obtained the captioned compound. Yield 0.03 g.

IR(KBr, cm⁻¹): 3400, 1760, 1710, 1600, 1400, 1330.

NMR(100 MHz, d₆-DMSO, β): 3.12 & 3.43 (ABq, J=18 Hz, 2-CH₂), 3.47 & 3.66 (ABq, J=14 Hz, CH₂CO), 4.70 & 4.87 (ABq, J=13 Hz, 3-CH₂), 4.91(d, J=5 Hz, 6-H), 5.50 (dd, J=5 & 9 Hz, 7-H), 6.47 (broad s, OCONH₂), 6.68 (s, thiazoline 5-H), 7-8 (broad, 1H, HN=).

NMR(100 MHz, D₂O, β): 3.46 & 3.77 (ABq, J=18 Hz, 2-CH₂), 3.85(s, CH₂CO), 4.80 & 5.00 (ABq, J=12 Hz, 3-CH₂), 5.24 (d, J=5 Hz, 6-H), 5.81 (d, J=5 Hz, 7-H), 6.82 (s, thiazoline 5-H).

UVλmax(H₂O, ε): 264 nm (1.27×10⁴)

Elemental analysis: Calcd. for C₁₄H₁₄N₅O₇S₂Na•2-H₂O C; 34.50, H; 3.72, N; 14.37. Found: C; 34.58, H; 3.83, N; 13.75.

| Minimum Inhibitory Concentrations (mcg/ml, agar dilution) | | | |
|---|---|---|---|
| Strain of Bacterium | Present compound | Cephaloridine | Cefazolin |
| E. coli NIHJ | 0.20 | 6.25 | 1.56 |
| E. coli 0-111 | 0.10 | 3.13 | 1.56 |
| E. coli T-7 | 1.56 | >100 | >100 |
| K. pneumoniae DT | 0.20 | 3.13 | 1.56 |
| K. pneumoniae GN 3835 | 0.20 | 50 | 12.5 |
| P. vulgaris IFO 3988 | 0.39 | 6.25 | 3.13 |
| P. mirabilis GN 4359 | 0.20 | 3.13 | 3.13 |
| P. morganii IFO 3168 | 0.78 | >100 | >100 |
| P. rettgeri 8 (TNO 336) | ≦0.012 | 1.56 | 0.20 |
| P. rettgeri CN 4733 | 0.20 | >100 | >100 |
| Ent. cloacae IFO 12937 | 50 | >100 | >100 |
| Cit. freundii GN 99 | 0.78 | 50 | 50 |
| Cit. freundii GN 1706 | 3.13 | >100 | >100 |

| Comparative protection tests of the compounds of this invention and cephaloridine on infected mice | |
|---|---|
| Example No. whereby compound is obtained | ED$_{50}$* in mg/kg |
| 1 | 0.075 |
| 4 | 0.019 |
| 6 | 0.071 |
| 7 | 0.056 |
| 9 | 0.04 |
| 10 | 0.089 |
| 13 | 0.084 |
| cephaloridine | 2.60 |

*Test animals: male mice (ICR/SLC) 5 mice per group per single dose
Infection: intraperitoneally with Escherichia coli 0-111
Administration: a single subcutaneous dose immediately after challenge
Observation period: 7 days

EXAMPLE 14

Production of sodium
7-[2-(2-imino-3-hydroxy-4-thiazolin-4-yl)acetamido]-3-(carbamoyloxymethyl)-3-cephem-4-carboxylate (1) 7-(4-chloro-3-oxobutyrylamido)-3-(carbamoyloxymethyl)-3-cephem-4-carboxylic acid A solution of 37.8 g of diketene in 190 ml of methylene chloride is cooled to −60° C. and thereto 31.9 g of chlorine is introduced under stirring. Separately, 82.0 g of 7-amino-3-(carbamoyloxymethyl)-3-cephem-4-carboxylic acid and 66.8 g of triethylamine are dissolved in a mixed solution of 300 ml of dimethylformamide and 300 ml of methylene chloride and the solution is cooled to −25° C. To this solution is added the above reaction mixture dropwise at the rate of the reaction temperature not exceeding −18° C. After stirring at this temperature for 30 min, 1000 ml of methyl ethyl ketone, 600 ml of ethylacetate, 200 g of phosphoric acid and 750 ml of brine are added thereto and the mixture is stirred. The organic layer is separated, washed with brine and concentrated to dryness. The residue is mixed with 50 ml of ethylacetate and the powder formed is collected, whereupon the sub-titled compound is obtained. Yield 79.6 g.

IR(KBr, cm$^{-1}$): 1773, 1720, 1660, 1540, 1410, 1335.

NMR(100 MHz, d$_6$-DMSO, β): 3.42 & 3.66 (ABq, J=18 Hz, 2-CH$_2$), 3.60 (s, COCH$_2$CO), 4.56 (s, ClCH$_2$), 4.64 & 4.94 (ABq, J=13 Hz, 3-CH$_2$), 5.12 (d, J=5 Hz, 6-H), 5.68 (dd, J=5 & 8 Hz, 7-H), 6.52 (broad s, CONH$_2$), 9.02 (d, J=8 Hz, CONH).

(2) In 10 ml of dimethylacetamide are dissolved 3.13 g of above prepared 7-(4-chloro-3-oxobutyrylamido)-3-(carbamoyloxymethyl)-3-cephem-4-carboxylic acid and 0.776 g of potassium thiocyanate and the resultant solution is stirred at room temperature for 12 hours. Thereto is added 0.56 g of hydroxylamine hydrochloride and the solution is heated to 60° C. for 60 min. After cooling 40 ml of ether is mixed with the solution and the supernatant is discarded. To the residue is added 100 ml of ethylacetate and the vessel is scrubbed. The powder formed is collected with suction and dissolved in 20 ml of 10% sodium bicarbonate. The solution is subjected to column chromatography on polystyrene resin (Amberlite XAD-2) with water as the developer. The fractions containing the titled product are pooled and lyophilized. By the procedure is obtained the titled compound. Yield 1.08 g. The IR and NMR spectra of the sample were satisfactorily identical with those of the sample prepared in example 13.

EXAMPLE 15

Production of sodium
7-[2-(2-imino-3-hydroxy-4-thiazolin-4-yl)acetamido]-3-(3-methyl-1,2,4-thiadiazol-5-yl)thiomethyl-3-cephem-4-carboxylate In 20 ml of phosphate buffer (pH 6.4) is dissolved 0.482 g of 7-[2-(2-imino-3-hydroxy-4-thiazolin-4-yl)acetamido]3-acetoxymethyl-3-cephem-4-carboxylic acid together with 0.176 g of 3-methyl-1,2,4-thiadiazol-5-thiol and 0.168 g of sodium hydrogen carbonate and the solution is stirred at 70° C. for 3 hours. This reaction mixture is subjected to column chromatography on polystyrene resin (Amberlite XAD-2) and eluted with water and 20% ethanol. The fractions containing the contemplated compound are pooled, concentrated under reduced pressure and lyophilized. By the above procedure is obtained the captioned compound. Yield 0.17 g.

IR(KBr, cm$^{-1}$): 1765.

NMR(100 MHz, D$_2$O, β): 2.59 (s, CH$_3$), 3.43 & 3.76 (ABq, J=18 Hz, 2-CH$_2$), 3.76 (s, CH$_2$CO), 4.15 & 4.57 (ABq, J=14 Hz, 3-CH$_2$), 5.12 (d, J=4.5 Hz, 6-H), 5.70 (d, J=4.5 Hz, 7-H), 6.72 (s, thiazoline 5-H).

Elemental analysis: Calcd. for C$_{16}$H$_{15}$N$_6$O$_5$S$_4$.1.5-H$_2$O: C; 34.97, H; 3.30, N; 15.29. Found: C; 35.16, H; 3.28, N; 15.47.

| Minimum Inhibitory Concentrations mcg/ml, agar dilution) | | | |
|---|---|---|---|
| Strain of Bacterium | Present compound | Cephaloridine | Cefazolin |
| E. coli NIHJ | 0.39 | 6.25 | 1.56 |
| E. coli 0-111 | 0.1 | 3.13 | 1.56 |
| E. coli T-7 | 6.25 | >100 | >100 |
| K. pneumoniae DT | 0.1 | 3.13 | 1.56 |
| P. vulgaris IFO 3988 | 0.1 | 6.25 | 3.13 |
| P. mirabilis GN 4359 | 0.1 | 3.13 | 3.13 |
| P. morganii IFO 3168 | 1.56 | >100 | >100 |
| P. rettgeri 8 (TNO 336) | ≦0.012 | 1.56 | 0.20 |
| P. rettgeri GN 4733 | 0.2 | >100 | >100 |
| Cit. freundii GN 99 | 0.78 | 50 | 50 |
| Cit. freundii GN 1706 | 12.5 | >100 | >100 |

EXAMPLE 16

Production of sodium
7-[2-(2-imino-3-hydroxy-4-thiazolin-4-yl)acetamido]-3-(2-trifluoromethyl-1,3,4-thiadiazol-5-yl)thiomethyl-3-cephem-4-carboxylate The same procedure described in Example 15 is repeated except 0.186 g of 2-trifluoromethyl-1,3,4-thiadiazol-5-thiol is used in place of 3-methyl-1,2,4- thiadiazol-5-thiol. The procedure gives the captioned compound. Yield 0.084 g.

IR(KBr, cm$^{-1}$): 1760.

NMR(100 MHz, D$_2$O, β): 3.46 & 3.81 (ABq, J=18 Hz, 2-CH$_2$), 3.75 (s, CH$_2$CO), 4.19 & 4.61 (ABq, J=14 Hz, 3-CH$_2$), 5.13 (d, J=5 Hz, 6-H), 5.69 (d, J=5 Hz, 7-H), 6.72 (s, thiazoline 5-H).

Elemental analysis: Calcd. for C$_{16}$H$_{12}$F$_3$N$_6$O$_5$S$_3$·Na·3.5H$_2$O C; 31.62, H; 3.15, N; 13.83. Found: C; 31.44, H; 2.84, N; 13.40.

| Minimum Inhibitory Concentrations mcg/ml, agar dilution) | | | |
|---|---|---|---|
| Strain of Bacterium | Present compound | Cephaloridine | Cefazolin |
| E. coli NIHJ | 0.78 | 6.25 | 1.56 |
| E. coli 0-111 | 0.39 | 3.13 | 1.56 |
| E. coli T-7 | 12.5 | >100 | >100 |
| K. pneumoniae DT | 0.39 | 3.13 | 1.56 |
| P. vulgaris IFO 3988 | 0.2 | 6.25 | 3.13 |
| P. mirabilis GN 4359 | 0.78 | 3.13 | 3.13 |
| P. morganii IFO 3168 | 3.13 | >100 | >100 |
| P. rettgeri 8 (TNO 336) | ≦0.012 | 1.56 | 0.20 |
| P. rettgeri GN 4733 | 1.56 | >100 | >100 |
| Cit. freundii GN 99 | 0.78 | 50 | 50 |
| Cit. freundii GN 1706 | 6.25 | >100 | >100 |

EXAMPLE 17

Production of sodium 7-[2-(2-imino-3-hydroxy-4-thiazolin-4-yl)acetamido]-3-[1-(2-hydroxyethyl)-1H-tetrazol-5-yl]thiomethyl-3-cephem-4-carboxylate The same procedure described in Example 15 is repeated except 0.146 g of 1-(2-hydroxyethyl)-1H-tetrazol-2-thiol is used in place of 3-methyl-1,2,4-thiadiazol-5-thiol. The procedure gives the captioned compound. Yield 0.215 g.

IR(KBr, cm$^{-1}$): 1758.

NMR(100 MHz, D$_2$O, β): 3.45 & 3.80 (ABq, J=18 Hz, 2-CH$_2$), 3.78 (s, CH$_2$CO), 4.04 (t, CH$_2$O), 4.14 & 4.41 (ABq, J=13 Hz, 3-CH$_2$), 4.57 (t, tetrazole-CH$_2$—), 5.13 (d, J=5 Hz, 6-H), 5.65 (d, J=5 Hz, 7-H), 6.74 (s, thiazoline 5-H)

Elemental analysis: Calcd. for C$_{16}$H$_{17}$N$_8$O$_6$S$_3$Na·2·H$_2$O: C; 33.56, H; 3.70, N; 19.57. Found: C; 33.72, H; 3.76, N; 18.28.

| Minimum Inhibitory Concentrations mcg/ml, agar dilution) | | | |
|---|---|---|---|
| Strain of Bacterium | Present compound | Cephaloridine | Cefazolin |
| E. coli NIHJ | 0.1 | 6.25 | 1.56 |
| E. coli 0-111 | 0.05 | 3.13 | 1.56 |
| E. coli T-7 | 1.56 | >100 | >100 |
| K. pneumoniae DT | 0.05 | 3.13 | 1.56 |
| K. pneumoniae GN 3835 | 0.1 | 50 | 12.5 |
| P. vulgaris IFO 3988 | 0.2 | 6.25 | 3.13 |
| P. mirabilis GN 4359 | 0.1 | 3.13 | 3.13 |
| P. morganii IFO 3168 | 0.39 | >100 | >100 |
| P. rettgeri 8 (TNO 336) | ≦0.012 | 1.56 | 0.20 |
| P. rettgeri GN 4733 | 0.05 | >100 | >100 |
| Cit. freundii GN 99 | 0.39 | 50 | 50 |
| Cit. freundii GN 1706 | 12.5 | >100 | >100 |

What is claimed is:

1. A cephalosporin derivative of the formula:

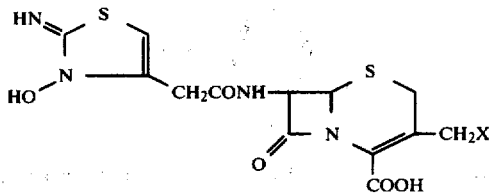

wherein X is hydrogen, hydroxyl, an acyloxy selected from the group consisting of alkylcarbonyloxy group of 2 to 4 carbon atoms; acetyloxy group substituted by an alkylcarbonyl group of 2 to 4 carbon atoms; phenylacetyloxy group which may be substituted at the α-position by hydroxyl, sulfo or amino group; alkylcarbonyloxy group of 2 to 4 carbon atoms as substituted by a carboxyl group; and a group of the formula:

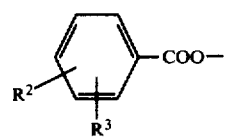

wherein R$^2$ and R$^3$, respectively, represent hydrogen, carboxyl, carboethoxycarbamoyl carboethoxysulfamoyl or nitro, alkoxy containing from 1 to 4 carbon atoms, carbamoyloxy or a quaternary ammonium group of the formula:

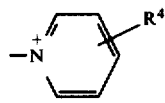

wherein R$^4$ is hydrogen, methyl, carbamoyl, carboxy, sulfonic or methoxy, or a pharmaceutically acceptable salt or ester thereof.

2. A cephalosporin derivative as claimed in claim 1, wherein X is acyloxy or carbamoyloxy.

3. A cephalosporin derivative as claimed in claim 2, wherein X is alkylcarbonyloxy having 2 to 4 carbon atoms.

4. A cephalosporin derivative according to claim 3, namely 7-[2-(2-imino-3-hydroxy-4-thiazolin-4-yl)acetamido]-3-acetoxymethyl-3-cephem-4-carboxylic acid or a pharmaceutically acceptable salt thereof.

5. A cephalosporin derivative as claimed in claim 2, wherein X is acetyloxy substituted with alkylcarbonyl having 2 to 4 carbon atoms.

6. A cephalosporin derivative as claimed in claim 2, wherein X is phenylacetyloxy which may be substituted at α-position with hydroxyl, sulfo or amino group.

7. A cephalosporin derivative according to claim 6, namely 7-[2-(2-imino-3-hydroxy-4-thiazolin-4-yl)acetamido]-3-mandeloxymethyl-3-cephem-4-carboxylic acid or a salt thereof.

8. A cephalosporin derivative as claimed in claim 2, wherein X is alkylcarbonyloxy having 2 to 4 carbon atoms which is substituted with carboxyl group.

9. A cephalosporin derivative as claimed in claim 2, wherein X is a group of the formula:

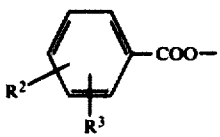

wherein each of $R^2$ and $R^3$ is hydrogen, carboxyl, carboethoxycarbamoyl, carboethoxysulfamoyl or nitro.

10. A cephalosporin derivative as claimed in claim 1, wherein X is carbamoyloxy, namely 7-[2-(2-imino-3-hydroxy-4-thiazolin-4-yl)acetamido]-3-(carbamoyloxymethyl)-3-cephem-4-carboxylic acid, or a pharmaceutically acceptable salt thereof.

11. A cephalosporin derivative as claimed in claim 1, wherein $R^4$ is carbamoyl, namely 7-[2-(2-imino-3-hydroxy-4-thiazolin-4-yl)acetamido]-3-(4-carbamoylpyridinium)methyl-3-cephem-4-carboxylic acid or a pharmaceutically acceptable salt thereof.

12. A pharmaceutical antibiotic composition containing a therapeutically effective amount of the compound claimed in claim 1 together with a pharmaceutically acceptable excipient or diluent therefor.

* * * * *